(12) United States Patent
Robertson et al.

(10) Patent No.: US 7,923,206 B2
(45) Date of Patent: *Apr. 12, 2011

(54) METHOD OF DETERMINING A CELLULAR RESPONSE TO A BIOLOGICAL AGENT

(75) Inventors: Barbara Robertson, Boulder, CO (US); Devin Leake, Denver, CO (US); Kathryn Robinson, Golden, CO (US); William S. Marshall, Boulder, CO (US); Anastasia Khvorova, Boulder, CO (US)

(73) Assignee: Dharmacon, Inc., Lafayette, CO (US)

( * ) Notice: Subject to any disclaimer, the term of this patent is extended or adjusted under 35 U.S.C. 154(b) by 658 days.

This patent is subject to a terminal disclaimer.

(21) Appl. No.: 11/283,481

(22) Filed: Nov. 18, 2005

(65) Prior Publication Data

US 2006/0110766 A1    May 25, 2006

Related U.S. Application Data

(60) Provisional application No. 60/630,320, filed on Nov. 22, 2004, provisional application No. 60/678,165, filed on May 4, 2005.

(51) Int. Cl.
*C12Q 1/68* (2006.01)
*C07H 21/02* (2006.01)
*C07H 21/04* (2006.01)

(52) U.S. Cl. .......... 435/6; 536/23.1; 536/24.1; 536/24.5

(58) Field of Classification Search ..................... None
See application file for complete search history.

(56) References Cited

U.S. PATENT DOCUMENTS

| | | |
|---|---|---|
| 4,924,624 A | 5/1990 | Suhadolnik et al. |
| 5,023,243 A | 6/1991 | Tullis |
| 5,138,045 A | 8/1992 | Cook et al. |
| 5,151,510 A | 9/1992 | Stec et al. |
| 5,166,320 A | 11/1992 | Wu et al. |
| 5,214,136 A | 5/1993 | Lin |
| 5,264,562 A | 11/1993 | Matteucci |
| 5,264,564 A | 11/1993 | Matteucci |
| 5,286,717 A | 2/1994 | Cohen |
| 5,399,676 A | 3/1995 | Froehler |
| 5,414,077 A | 5/1995 | Lin |
| 5,434,257 A | 7/1995 | Matteucci |
| 5,457,191 A | 10/1995 | Cook |
| 5,457,527 A | 10/1995 | Manns et al. |
| 5,459,255 A | 10/1995 | Cook |
| 5,484,908 A | 1/1996 | Froehler et al. |
| 5,487,872 A | 1/1996 | Hafeman et al. |
| 5,489,677 A | 2/1996 | Sanghvi |
| 5,502,177 A | 3/1996 | Matteucci |
| 5,514,786 A | 5/1996 | Cook |
| 5,532,130 A | 7/1996 | Alul |
| 5,578,718 A | 11/1996 | Cook |
| 5,580,767 A | 12/1996 | Cowsert |
| 5,587,361 A | 12/1996 | Cook |
| 5,587,469 A | 12/1996 | Cook |
| 5,587,470 A | 12/1996 | Cook |
| 5,591,721 A | 1/1997 | Agrawal |
| 5,594,121 A | 1/1997 | Froehler |
| 5,596,086 A | 1/1997 | Matteucci |
| 5,608,046 A | 3/1997 | Cook |
| 5,610,289 A | 3/1997 | Cook |
| 5,614,617 A | 3/1997 | Cook |
| 5,635,488 A | 6/1997 | Cook |
| 5,637,573 A | 6/1997 | Agrawal |
| 5,644,048 A | 7/1997 | Yau |
| 5,645,985 A | 7/1997 | Froehler |
| 5,652,355 A | 7/1997 | Metelev et al. |
| 5,652,356 A | 7/1997 | Agrawal |
| 5,658,731 A | 8/1997 | Sproat |
| 5,670,633 A | 9/1997 | Cook |
| 5,674,108 A | 10/1997 | Rolle |
| 5,674,908 A | 10/1997 | Haces et al. |
| 5,677,437 A | 10/1997 | Teng |
| 5,681,941 A | 10/1997 | Cook |
| 5,708,161 A | 1/1998 | Reese |
| 5,734,041 A | 3/1998 | Just |
| 5,750,666 A | 5/1998 | Caruthers |
| 5,756,710 A | 5/1998 | Stein |
| 5,757,710 A | 5/1998 | Li et al. |
| 5,763,588 A | 6/1998 | Matteucci |
| 5,767,264 A | 6/1998 | Otlvos |

(Continued)

FOREIGN PATENT DOCUMENTS

EP    1114623    10/2001

(Continued)

OTHER PUBLICATIONS

U.S. Appl. No. 11/283,484, filed Nov. 18, 2005, Robertson et al.
U.S. Appl. No. 11/283,482, filed Nov. 18, 2005, Robertson et al.
U.S. Appl. No. 11/283,483, filed Nov. 18, 2005, Robertson et al.
Silva et al., RNA Interference Microarrays, High-Throughput Loss-of-Function Genetics in Mammalian Cells. PNAS. Apr. 27, 2004, vol. 101, No. 17, pp. 6548-6552.
VanHecke et al., High-Throughput Gene Silencing Using Cell Arrays, Oncogene, 2004, vol. 23, pp. 8353-8358.
Mousses et al., PNAi Microarry Analysis in Cultured Mammalian Cells, Genome Research, 2003, vol. 13, pp. 2341-2347.
Kumar et al., High-throughput selection of effective RNAi probes for gene silencing, Genome Research, 2003, vol. 13, pp. 2333-2340.

(Continued)

*Primary Examiner* — Sean R McGarry
(74) *Attorney, Agent, or Firm* — Workman Nydegger

(57) ABSTRACT

A method of determining a cellular response to a biological agent can be preformed in the presence of gene silencing. Such a method can include the use of siRNA in order to silence various genes in the cell in order to monitor the cellular response to the biological agent when a gene has been silenced. Accordingly, the response of a cell having a silenced gene to a biological agent can be indicative of which genes may be responsible for normal or abnormal cellular responses to various synthetic and natural biological agents such as active agents or pathogens.

23 Claims, 9 Drawing Sheets

U.S. PATENT DOCUMENTS

| | | |
|---|---|---|
| 5,770,713 A | 6/1998 | Imbach |
| 5,773,601 A | 6/1998 | Agrawal |
| 5,777,092 A | 7/1998 | Cook et al. |
| 5,792,844 A | 8/1998 | Sanghvi |
| 5,792,847 A | 8/1998 | Bhur |
| 5,811,274 A | 9/1998 | Palsson |
| 5,811,534 A | 9/1998 | Cook |
| 5,817,781 A | 10/1998 | Swaminathan |
| 5,830,653 A | 11/1998 | Froehler |
| 5,834,439 A | 11/1998 | Haces et al. |
| 5,834,607 A | 11/1998 | Manoharan |
| 5,849,902 A | 12/1998 | Arrow |
| 5,852,182 A | 12/1998 | Cook |
| 5,852,188 A | 12/1998 | Cook |
| 5,856,455 A | 1/1999 | Cook |
| 5,859,221 A | 1/1999 | Cook |
| 5,872,232 A | 2/1999 | Cook |
| 5,883,237 A | 3/1999 | Stec |
| 5,889,136 A | 3/1999 | Scaringe et al. |
| 5,898,031 A | 4/1999 | Crooke |
| 5,912,339 A | 6/1999 | Miller |
| 5,914,396 A | 6/1999 | Cook |
| 5,919,619 A | 7/1999 | Tullis |
| 5,948,903 A | 9/1999 | Cook |
| 5,965,722 A | 10/1999 | Ecker |
| 5,973,136 A | 10/1999 | Agrawal |
| 5,989,835 A | 11/1999 | Dunlay et al. |
| 5,989,912 A | 11/1999 | Arrow |
| 5,998,203 A | 12/1999 | Matulic-adamic |
| 5,998,206 A | 12/1999 | Cowsert |
| 6,005,087 A | 12/1999 | Cook |
| 6,005,094 A | 12/1999 | Simon |
| 6,005,096 A | 12/1999 | Matteucci |
| 6,007,992 A | 12/1999 | Lin |
| 6,008,400 A | 12/1999 | Scaringe et al. |
| 6,028,183 A | 2/2000 | Lin |
| 6,043,352 A | 3/2000 | Manoharan |
| 6,060,592 A | 5/2000 | Acevedo |
| 6,110,916 A | 8/2000 | Haces et al. |
| 6,111,085 A | 8/2000 | Cook |
| 6,111,086 A | 8/2000 | Scaringe |
| 6,114,513 A | 9/2000 | Cook |
| 6,127,533 A | 10/2000 | Cook |
| 6,140,482 A | 10/2000 | Lyer |
| 6,143,881 A | 11/2000 | Metelev |
| 6,147,200 A | 11/2000 | Manoharan |
| 6,153,737 A | 11/2000 | Manoharan |
| 6,166,188 A | 12/2000 | Cook |
| 6,166,197 A | 12/2000 | Cook et al. |
| 6,172,209 B1 | 1/2001 | Manoharan |
| 6,197,944 B1 | 3/2001 | Walder |
| 6,204,027 B1 | 3/2001 | Goodchild |
| 6,222,025 B1 | 4/2001 | Cook |
| 6,235,886 B1 | 5/2001 | Manoharan |
| 6,239,265 B1 | 5/2001 | Cook |
| 6,242,589 B1 | 6/2001 | Cook |
| 6,242,591 B1 | 6/2001 | Cole |
| 6,265,558 B1 | 7/2001 | Cook |
| 6,271,358 B1 | 8/2001 | Manoharan |
| 6,277,967 B1 | 8/2001 | Manoharan |
| 6,277,982 B1 | 8/2001 | Fraser et al. |
| 6,300,319 B1 | 10/2001 | Manoharan |
| 6,307,040 B1 | 10/2001 | Cook |
| 6,322,987 B1 | 11/2001 | Cook |
| 6,326,358 B1 | 12/2001 | Manoharan |
| 6,331,441 B1 | 12/2001 | Balch et al. |
| 6,335,437 B1 | 1/2002 | Manoharan |
| 6,346,614 B1 | 2/2002 | Metelev |
| 6,348,312 B1 | 2/2002 | Peyman |
| 6,358,931 B1 | 3/2002 | Cook |
| 6,359,124 B1 | 3/2002 | Ecker |
| 6,369,040 B1 | 4/2002 | Acevedo |
| 6,369,209 B1 | 4/2002 | Manoharan |
| 6,380,368 B1 | 4/2002 | Froehler |
| 6,391,636 B1 | 5/2002 | Monia |
| 6,395,492 B1 | 5/2002 | Manoharan et al. |
| 6,399,297 B1 | 6/2002 | Baker |
| 6,399,663 B1 | 6/2002 | Haces et al. |
| 6,403,781 B2 | 6/2002 | Cole |
| 6,410,702 B1 | 6/2002 | Swaminathan |
| 6,414,127 B1 | 7/2002 | Lin |
| 6,416,959 B1 | 7/2002 | Giuliano et al. |
| 6,420,546 B1 | 7/2002 | Seliger |
| 6,440,943 B1 | 8/2002 | Cook |
| 6,447,998 B1 | 9/2002 | Froehler |
| 6,451,991 B1 | 9/2002 | Martin |
| 6,458,940 B2 | 10/2002 | Roberts |
| 6,476,205 B1 | 11/2002 | Bhur |
| 6,485,974 B1 | 11/2002 | Popoff |
| 6,495,672 B1 | 12/2002 | Froehler |
| 6,506,559 B1 | 1/2003 | Fire et al. |
| 6,514,464 B1 | 2/2003 | Knebel |
| 6,525,031 B2 | 2/2003 | Manoharan |
| 6,531,584 B1 | 3/2003 | Cook |
| 6,534,639 B1 | 3/2003 | Manoharan |
| 6,544,790 B1 | 4/2003 | Sabatini |
| 6,573,039 B1 | 6/2003 | Dunlay et al. |
| 6,576,752 B1 | 6/2003 | Manoharan et al. |
| 6,590,093 B1 | 7/2003 | Scaringe |
| 6,600,032 B1 | 7/2003 | Manoharan |
| 6,608,035 B1 | 8/2003 | Agrawal |
| 6,620,591 B1 | 9/2003 | Dunlay et al. |
| 6,624,293 B1 | 9/2003 | Agrawal |
| 6,645,943 B1 | 11/2003 | Agrawal |
| 6,653,458 B1 | 11/2003 | Manoharan |
| 6,671,624 B1 | 12/2003 | Dunlay et al. |
| 6,673,611 B2 | 1/2004 | Thompson |
| 6,677,445 B1 | 1/2004 | Innis |
| 6,683,167 B2 | 1/2004 | Metelev |
| 6,716,582 B2 | 4/2004 | Gonye et al. |
| 6,716,588 B2 | 4/2004 | Sammak et al. |
| 6,716,882 B2 | 4/2004 | Haces et al. |
| 6,759,206 B1 | 7/2004 | Rubin et al. |
| 6,809,193 B2 | 10/2004 | McKay |
| 6,811,975 B2 | 11/2004 | Cook |
| 6,841,542 B2 | 1/2005 | Bartlemez |
| 6,846,921 B2 | 1/2005 | Innis |
| 6,875,578 B2 | 4/2005 | Giuliano et al. |
| 6,881,831 B2 | 4/2005 | Lyer |
| 6,902,883 B2 | 6/2005 | Dunlay et al. |
| 6,924,109 B2 | 8/2005 | Melcher et al. |
| 6,936,467 B2 | 8/2005 | Kmiec |
| 6,951,757 B2 * | 10/2005 | Sabatini ............... 435/455 |
| 6,958,239 B2 | 10/2005 | Arrow |
| 6,977,245 B2 | 12/2005 | Klinman |
| 6,998,206 B2 | 2/2006 | Fuller et al. |
| 7,045,609 B2 | 5/2006 | Metelev |
| 7,067,497 B2 | 6/2006 | Hanecak |
| 7,078,196 B2 | 7/2006 | Tuschl |
| 7,173,014 B2 | 2/2007 | Agrawal |
| 7,595,387 B2 | 9/2009 | Leake et al. |
| 2002/0006664 A1 | 1/2002 | Sabatini |
| 2002/0128466 A1 | 9/2002 | Cole |
| 2002/0160379 A1 | 10/2002 | Cook |
| 2003/0036516 A1 | 2/2003 | Agrawal |
| 2003/0045698 A1 | 3/2003 | Manoharan |
| 2003/0096770 A1 | 5/2003 | Krotz |
| 2003/0135033 A1 | 7/2003 | Klippel-Giese |
| 2003/0170642 A1 | 9/2003 | Caldwell et al. |
| 2003/0170891 A1 | 9/2003 | McSwiggen |
| 2003/0190626 A1 | 10/2003 | Ravikumar |
| 2003/0203486 A1 | 10/2003 | Sabatini |
| 2003/0206887 A1 * | 11/2003 | Morrissey et al. ........... 424/93.2 |
| 2003/0228601 A1 | 12/2003 | Sabatini |
| 2003/0228694 A1 | 12/2003 | Sabatini |
| 2004/0009938 A1 | 1/2004 | Manoharan |
| 2004/0014108 A1 | 1/2004 | Eldrup |
| 2004/0014956 A1 | 1/2004 | Woolf |
| 2004/0014957 A1 | 1/2004 | Eldrup |
| 2004/0019008 A1 | 1/2004 | Lewis et al. |
| 2004/0043948 A1 | 3/2004 | Baker |
| 2004/0053875 A1 | 3/2004 | Kruetzer |
| 2004/0054155 A1 | 3/2004 | Woolf |
| 2004/0058886 A1 | 3/2004 | Scaringe |
| 2004/0072779 A1 | 4/2004 | Kruetzer |
| 2004/0096880 A1 | 5/2004 | Kmiec |
| 2004/0102408 A1 | 5/2004 | Kruetzer |

| | | | |
|---|---|---|---|
| 2004/0110296 A1 | 6/2004 | Vargeese | |
| 2004/0137064 A1 | 7/2004 | Lewis et al. | |
| 2004/0147022 A1 | 7/2004 | Baker | |
| 2004/0147023 A1 | 7/2004 | Baker | |
| 2004/0167090 A1 | 8/2004 | Monaharan | |
| 2004/0180351 A1 | 9/2004 | Giese | |
| 2004/0198640 A1 | 10/2004 | Leake | |
| 2004/0204420 A1 | 10/2004 | Rana | |
| 2004/0248299 A1 | 12/2004 | Jayasena | |
| 2004/0259247 A1* | 12/2004 | Tuschl et al. | 435/375 |
| 2004/0266707 A1 | 12/2004 | Leake et al. | |
| 2005/0020521 A1 | 1/2005 | Rana | |
| 2005/0020525 A1 | 1/2005 | McSwiggen | |
| 2005/0026160 A1 | 2/2005 | Allerson | |
| 2005/0059044 A1 | 3/2005 | Graham | |
| 2005/0130181 A1 | 6/2005 | McSwiggen | |
| 2005/0181385 A1* | 8/2005 | Linsley et al. | 435/6 |
| 2005/0223427 A1 | 10/2005 | Leake | |
| 2005/0239728 A1 | 10/2005 | Pachuk et al. | |
| 2005/0255487 A1 | 11/2005 | Khorova | |
| 2006/0110829 A1 | 5/2006 | Robertson et al. | |
| 2006/0115461 A1 | 6/2006 | Robertson et al. | |
| 2006/0127891 A1 | 6/2006 | McSwiggen | |
| 2006/0166234 A1 | 7/2006 | Robertson et al. | |
| 2006/0178324 A1 | 8/2006 | Hadwiger | |
| 2006/0223777 A1 | 10/2006 | Vermeulen | |
| 2007/0141134 A1 | 6/2007 | Kosak | |
| 2007/0167384 A1 | 7/2007 | Leake | |
| 2007/0173476 A1 | 7/2007 | Leake | |
| 2007/0269889 A1 | 11/2007 | Leake | |

FOREIGN PATENT DOCUMENTS

| | | |
|---|---|---|
| EP | 1389637 | 2/2004 |
| EP | 1559785 | 8/2005 |
| EP | 1814895 | 8/2007 |
| WO | 93-04204 | 3/1993 |
| WO | 94-01550 | 1/1994 |
| WO | 94-21825 | 9/1994 |
| WO | 94-26887 | 11/1994 |
| WO | WO 97/30731 | 8/1997 |
| WO | WO9742819 | 11/1997 |
| WO | 99-32619 | 7/1999 |
| WO | WO0012454 | 3/2000 |
| WO | WO0120015 | 3/2001 |
| WO | 01-75164 | 10/2001 |
| WO | 02-044321 | 6/2002 |
| WO | 02-094185 | 11/2002 |
| WO | 03-064625 | 8/2003 |
| WO | 03-064626 | 8/2003 |
| WO | 03-070193 | 8/2003 |
| WO | 03-070918 | 8/2003 |
| WO | 03-072705 A2 | 9/2003 |
| WO | 03-072705 A3 | 9/2003 |
| WO | 03-074654 | 9/2003 |
| WO | WO 2004/009847 | 1/2004 |
| WO | 2004-015107 A2 | 2/2004 |
| WO | 2004-015107 A3 | 2/2004 |
| WO | WO2004011624 | 2/2004 |
| WO | WO2004045543 | 6/2004 |
| WO | 2004-080406 | 9/2004 |
| WO | WO2004078946 | 9/2004 |
| WO | 2004-091515 | 10/2004 |
| WO | WO2004090105 | 10/2004 |
| WO | 2004-109290 | 12/2004 |
| WO | 2005-019453 | 3/2005 |
| WO | WO 2005/039645 | 5/2005 |
| WO | WO2005078094 | 8/2005 |
| WO | WO2005097992 | 10/2005 |
| WO | WO 2006/058046 | 6/2006 |
| WO | WO 2006/058048 | 6/2006 |
| WO | WO 2006/060246 | 6/2006 |
| WO | WO 2006/071410 | 7/2006 |

OTHER PUBLICATIONS

Mousses et al., RNAi microarray analysis in cultured mammalian cells, Genome Research, 2003, vol. 13, pp. 2341-2347.
Bailey et al, Applications of transfected cell microarrays in high-throughput drug discovery, Drug Discovery Today, 2002, vol. 7, pp. S113-S118.
Homna et al., The role of atelococollagen-based cell transfection arry in high-throughput screening of gene functions and in drug discover, Current Drug Discovery Technologies, Dec. 2004, vol. 1, pp. 287-294.
Office Action dated Mar. 21, 2007 from U.S. Appl. No. 11/283,484 (Robertson et al.), 15 pages.
International Search Report from PCT/US2005/042404, Mar. 7, 2007, 2 pages.
International Preliminary Report on Patentability from PCT/US2006/042404, May 22, 2007, 5 pages.
Written Opinion from PCT/US2006/042404, Mar. 7, 2007, 4 pages.
International Search Report from PCT/US2005/042403, Sep. 28, 2006, 4 pages.
International Preliminary Report on Patentability from PCT/US2005/042403, May 22, 2007, 4 pages.
Written Opinion from PCT/US2005/042403, Jun. 8, 2006, 3 pages.
International Search Report from PCT/US2005/042385, Apr. 5, 2007, 3 pages.
International Preliminary Report on Patentability from PCT/US2005/042385, May 22, 2007, 4 pages.
Written Opinion from PCT/US2005/042385 Jan. 29, 2007, 3 pages.
International Search Report from PCT/US2005/042407, Sep. 8, 2006, 2 pages.
International Preliminary Report on Patentability from PCT/US2005/042407, May 22, 2007, 4 pages.
Written Opinion from PCT/US2005/042407, Jun. 20, 2006, 3 pages.
Vermeulen, A. et al., "The contributions of dsRNA structure to Dicer specificity and efficiency"; RNA,11:674-682 (2005).
*Atlas Venture*, Dharmacon and Akceli Announce Research Collaboration to Combine Reverse Transfection and siRNA for High Throughput Gene Silencing, www.atlasventure.com/home/news_content.asp?ne_id=1741 (Aug. 24, 2004).
*Ambion*, High Throughput siRNA Deliery In Vitro: From Cell Lines to Pimrary Cells, TechNotes 12(2); ww.ambion.com/techlib/tn/122/3.html (downloaded Jul. 18, 2005).
*Boston Business Journal*, "Biotech firm Akceli wins first patent," www.bizhournals.com/boston/stories/2003/04/07/daily13.html.
Dhellin, Olivier et al., "Functional differences between the human LINE retrotransposon and retroviral revsere transcriptases for in vivo mRNA reverse transcription," The EMBO Journal, vol. 16, pp. 6590-6602; 1997.
Press Release, Dharmacon Launches siArray RTF™ siRNA Libraries—First-Ever Using Reverse Transfection Technology, qb Perbio Solutions for Life Science; Layfayette, Colo.; Apr. 22, 2005.
Hannon, Gregory J., "RNA Interference," Nature, vol. 418; Jul. 11, 2002. (www.nature.com/nature).
Ketting, R.F. et al. (2001) Dicer Functions in RNA Interference and in Synthesis of Small RNA Involved in Developmental Timing in C. elegans Genes Dev., Oct. 15, 2001, 15(20):2654-9.
Paddison, P. J., et al., "A resource for large-scale RNA-interference-based screens in mammals," Nature, vol. 428; Mar. 25, 2004 (www.nature.com/nature).
He, L. et al., "MicroRNAs: Small RNAs with a Big Role in Gene Regulation," Nature, vol. 5, pp. 522-532; Jul. 2004 (www.nature.com/reviews/genetics).
Hannon, G.J., et al., "Unlocking the Potential of the Human Genome with RNA Interference," Nature, vol. 431; Sep. 16, 2004 (www.nature.com/nature).
Hammond, S.M., et al., "Post-Transcriptional Gene Silencing by Double-Stranded RNA," Nature, vol. 2; Feb. 2001 (www.nature.com/reviews/genetics).
Hannon, G., "Growth control in mammalian cells: post-transcriptional gene silencing," (www.cshl.org/public/SCIENCE/hannon.html) (2004).
Denli, A.M., et al., "RNAi: an ever-growing puzzle," *TRENDS in Biochemical Sciences*, vol. 28, No. 4, Apr. 2003.
Silva, J.M., et al., "RNA interference: a promising approach to antiviral therapy?" *Trends in Molecular Medicine*, vol. 8, No. 11, Nov. 2002.
Qiagen Website (www.qiagen.com), Transfection Cell Database, Using siRNA (dsRNA) as Nucleic Acid, Cell Records.

"The HiPerformance algorithm designs highly potent and specific siRNA", Technical Information, www1.qiagen.com/literature/resources/RNAi/1030174_TI_GS_siRNA_0105.-pdf; downloaded Jul. 18, 2005.
Ziauddin, J. et al., "Microarrays of cells expressing defined cDNAs," Letters to Nature, Nature, 411, pp. 107-110 (May 3, 2001); doi:10.1038/35075114.
Reverse Transfection Homepage and Guide, Ziauddin, J. and Sabatini, D., http://staffa.wi.mit.edu/sabatini_public/reverse/transfection/content (downloaded Aug. 24, 2004).
Product Insert, siARRAY™ siRNA Libraries, Version 2.0; Dharmacon RNA Technologies.
SuperArray Bioscience Corporation, Introducing siRNA Array Plates, www.supperarray.com/RNAiArrayPlates.php (downloaded Jul. 18, 2005).
SuperArray Bioscience Corporation, siRNA Array Plates, www.supperarray.com/manuals/Present_ArrayPlates.pdf (downloaded Jul. 18, 2005).
SuperArray Bioscience Corporation, Newly Released SureSilencing™ Mouse siRNA Products, www.supperarray.com/siRNAnew.php?sp=Mouse (downloaded Jul. 18, 2005).
SuperArray Bioscience Corporation, Newly Released SureSilencing™ Human siRNA Products, www.supperarray.com/siRNAnew.php?sp=Human (downloaded Jul. 18, 2005).
Qiagen, Transfection Reagent Selector Kit Handbook, Jan. 1999.
Bernstein, E., et al., "The rest is silence," RNA (2001), 7:1509-1521. Cambridge University Press.
SuperArray SureSilencing Array Plates User Manual (Version 1.0 Feb. 13, 2004)—SureSilencing Array Plates; Validated Gene-Specific siRNA For Pathway Profiling By Reverse Transfection; Frederick, MD, USA.
SuperArray SureSilencing Array Plates User Manual (Version 1.1 Mar. 5, 2004)—SureSilencing Array Plates; Validated Gene-Specific Specific siRNA For Pathway Profiling By Reverse Transfection; Frederick, MD, USA.
U.S. Appl. No. 11/857,732, filed Sep. 19, 2007, Khvorova.
Amarzguioui et al., Tolerance for Mutations and Chemical Modifications in siRNA, 2003, Nucleic Acids Research, vol. 31, No. 2, pp. 589-595 Oxford University Press.
Parrish et al., Functional Anatomy of a dsRNA Trigger: Differential Requirement for the Two Trigger Strands in RNA Interference, Nov. 2000, Molecular Cell, vol. 6, pp. 1077-1087.
Elbashir et al., RNA Interference is Mediated by 21- and 22-Nucleotide RNAs, Jan. 2001, Genes & Development, vol. 15, pp. 188-200.
Letsinger et al., Cholesteryl-conjugated Oligonucleotides: Synthesis, properties, and activity as inhibitors of replication of human immunodeficiency virus in cell culture, Sep. 1989, Proc. Natl. Acad. Sci. vol. 86, pp. 6553-6556.
Boiziau et al. (1995) Antisense 2"-O-alkyl Oligoribinucleotides are efficient inhibitors of reverse transcription, Nucleic Acids Res. 23/1:64-71.
Chiu et al. (2003) siRNA function in RNAi: A Chemical Modification Analysis, RNA 9/9:1034-1048.
Conrad et al. (1995) Enzymatic synthesis of 2'-modified nucleic acids: identification of important phosphate and ribose moieties in Rnase P substrates, Nucleic Acids Res. 23/11:1845-1853.
Czauderna et al. (2003) Structural Variations and Stabilizing modifications of synthetic siRNAs in mammalian cells, Nucleic Acids Res. 31/11:2705-2716.
Grunweller et al. (2003) Comparison of different antisense strategies in mammalian cells using locked nucleic acid, 2'-O-methyl RNA, phosphorothioates and small interfering RNA, Nucleic Acids Res. 31/12:3185-3193.
Holen et al. (2003) Similar behavior of single-strand and double-strand siRNAs suggests they act through a common RNAi pathway, Nucleic Acids Res. 31/9:2401-2407.
Johansson et al. (1994) Target-specific arrest of mRNA translation by antisense 2'-O-Alkyloligoribonucleotides, Nucleic Acids Res. 22/22:4591-4598.
Larrouy et al. (1995) Rnase H is responsible for the non-specific inhibition of in vitro translation by 2'-O-alkyl chimeric oligonucleotides: high affinity or selectivity, a dilemma to design antisense oligomers, Nucleic Acids Res. 23/17:3434-3440.
Liang, L. et al (2002) Optimizing the delivery systems of chimeric RNA-DNA oligonucleotides: Beyond general oligonucleotide transfer, Eur J. Biochem 269:5953-5758.
Majlessi et al. (1998) Advantages of 2'-O-methyl oligoribonucleotide probes for detecting RNA targets, Nuclic Acids Res.26/9:2224-2229.
Monia et al. (1993) Evaluation of 2'-Modified Oligonucleotides Containing 2'-Deoxy gaps as Antisense Inhibitors of Gens Expression, J. Biol. Chem. 268/19:14514-14522.
Nykanen et al. (2001) ATP Requirements and Small Interfering RNA Structure in the RNA Interference Pathway, Cell 107:309-321.
Stump et al. (1999) The use of modified primers to eliminate cycle sequencing artifacts, Nucleic Acids Res. 27/23:4642-4648.
Uchiyama et al. (1994) Studies of the Interactions Between Escherichia coli Ribonuclease HI and Its Substrate, J Mol. Biol. 243:782-791.
Braasch, D. et al (2003) "RNA Interference in Mammalian Cells by Chemically-modified RNA" Biochemistry 42/26:7967-7995.
Harborth, J. et al. (Apr. 2003) "Sequence, Chemical, and Structural Cariation of Small Interfering RNAs and Short Harpin RNAs and the Effect on Mammalian Gene Silencing" Antisense & Nucleic Acid Drug Development 13/2:83-105.
Elbashir, S. M. et al (2001) Functional Anatomy of siRNAs for Mediating efficient RNAi in Drosophila melanogaster embyro lysate, The EMBO Journal 20/23:6877-6888.
Jackson, A. L. et al. (2003) Expression Profiling Reveals off-target Gene Regulation by RNAI, Nature Biotechnology 21/6:635-637.
Lubini et al. Stabilizing effects of the RNA 2'-sustitutent Crystal Structure of an Oligodeoxynucleotide duplex Containing 2'-O-methylated adenosines. Chem. Biol. 1004 Sep. 1(1): 39-45.
Dharmacon RNA Technologies, Dharmacon and Merck's Rosetta Collaborate to Assess Multiple Factors Affecting Efficacy and Specificity of siRNA for Gene Silencing, Oct. 8, 2003, Press Release, Layfette, CO.
Rosetta siRNA Experiments Performed in 2007, pp. 1-11.
Rossi, J., "A Cholesterol Connection in RNAi," Nature, Nov. 2004, vol. 432, pp. 155-156.
Soutscheck, J., et al., "Therapeutic Silencing of an Endogenous Gene by Systemic Administration of Modified siRNAs," Nature, Nov. 2004, vol. 432, pp. 173-178.
Kim, D. H. et al., Synthetic dsRNA Dicer Substrates Enhance RNAi Patency and efficacy, Nature Biotechnology, Advanced Online Publication, (2004), p. 1-5, Published Online Dec. 26, 2004.
Paddison, Patrick J. et al., "Short hairpin RNAs"shRNAs) induce sequence-specific silencing in mammalian cells, Genes & Development 16, (2002), p. 946-958.
Zhang, Haidi et al., "Human Dicer Preferentially cleaves dsRNAs at their termini without a requirement for ATP", The EMBO Journal vol. 21, No. 21, (2002), p. 5875-5885.
Hohjoh, Hirohiko, "Enhancement of RNAi activity by improved siRNA duplexes", FEBS letters 557, (2004), p. 193-198.
Ma, Jin-Baio et al., "Structural basis for overhanging-specific small interfering RNA recognition by PAZ domain", Nature, vol. 429, May 20, 2004, p. 318-322.
Siolas, Despina, "Synthetic shRNAs as potent RNAi triggers", Nature Biotechnology, p. 1-5, published online Dec. 26, 2004.
Zeng, Yan et al., "Both Natural and Designed Micro RNAs Technique Can Inhibit the Expression of Cognate mRNAs When Expressed in Human Cells", Molecular Cell, vol. 9, Jun. 2002, p. 1327-1333.
Holen et al. (2002) Positional Effects of short interfering RNAs targeting the human coagulation trigger Tissue Factor, Nucleic Acid Research, 30/8:1757-1766.
International Search Report from PCT/US05/011008, Mar. 31, 2005, 5 Pages.
Written Opinion from PCT/US05/011008, Mar. 31, 2005, 6 Pages.
International Search Report from PCT/US05/003365, Apr. 2, 2005, 7 Pages.
Written Opinion from PCT/US05/003365, Apr. 2, 2005, 10 Pages.
Notification Regarding Review of Justification for Invitation to Pay Additional Fees from PCT/US05.003365, Apr. 2, 2005, 4 Pages.
Office Action dated Jul. 8, 2008 cited in U.S. Appl. No. 11/283,484.
Office Action dated Oct. 15, 2008 cited in U.S. Appl. No. 11/283,482.

Office Action dated Nov. 3, 2008 cited in U.S. Appl. No. 11/283,483.
Office Action dated Aug. 23, 2005 cited in U.S. Appl. No. 11/019,831.
Office Action dated Feb. 21, 2006 cited in U.S. Appl. No. 11/019,831.
Office Action dated Jun. 28, 2006 cited in U.S. Appl. No. 11/019,831.
Office Action dated Feb. 9, 2007 cited in U.S. Appl. No. 11/019,831.
Office Action dated Oct. 30, 2007 cited in U.S. Appl. No. 11/019,831.
Office Action dated Sep. 4, 2008 cited in U.S. Appl. No. 11/019,831.
Office Action dated Sep. 12, 2008 cited in U.S. Appl. No. 11/390,829.
Office Action dated Feb. 22, 2008 cited in U.S. Appl. No. 11/051,195.
Office Action dated Dec. 18, 2008 cited in U.S. Appl. No. 11/051,195.
Office Action dated Sep. 8, 2008 cited in U.S. Appl. No. 11/551,350.
Office Action dated Dec. 31, 2008 cited in U.S. Appl. No. 11/619,993.
Office Action dated Jan. 14, 2005 cited in U.S. Appl. No. 10/406,908.
Office Action dated Apr. 5, 2005 cited in U.S. Appl. No. 10/406,908.
Office Action dated Sep. 23, 2005 cited in U.S. Appl. No. 10/406,908.
Office Action dated Jan. 27, 2005 cited in U.S. Appl. No. 10/613,077.
Office Action dated Apr. 12, 2005 cited in U.S. Appl. No. 10/613,077.
Office Action dated Sep. 7, 2005 cited in U.S. Appl. No. 10/613,077.
Minakuchi, Yoshiko, et al., Atelocollagen-Mediated Synthetic Small Interfering RNA Delivery for Effective Gene Silencing In Vitro and In Vitro, Nucleic Acids Research, 2004, vol. 32, No. 13, Oxford University Press 2004, pp. 1-7, Published online Jul. 22, 2004.
Yoshikawa, Tomohiro, et al., Transfection Microarray of Human Mesenchymal Stem Cells and On-Chip siRNA Gene Knockdown, Journal of Controlled Release 96 (2004), pp. 227-232.
U.S. Appl. No. 11/283,482, filed Apr. 8, 2010, Office Action.
Office Action from U.S. Appl. No. 11/283,483, dated Dec. 11, 2007.
Office Action from U.S. Appl. No. 11/283,483, dated Nov. 3, 2008.
Office Action from U.S. Appl. No. 11/283,483, dated Dec. 28, 2009.
Office Action from U.S. Appl. No. 11/283,482, dated Apr. 8, 2010.
Notice of Allowance from U.S. Appl. No. 11/283,482, dated Aug. 23, 2010.
Notice of Allowance from U.S. Appl. No. 11/283,484, dated Aug. 12, 2010.
Extended European Search Report from EPO Application No. 05852038.8, dated Apr. 24, 2008.
Supplemental European Search Report from EPO Application No. 05852038.8, dated May 13, 2008.
Annex to EPO Form 2001A from EPO Application No. 05852038.8, dated Aug. 1, 2008.
Examination Report from EPO Application No. 05852038.8, dated Feb. 19, 2009.
Examination Report from EPO Application No. 05852038.8, dated Jun. 23, 2009.
Examination Report from EPO Application No. 05852038.8, dated Nov. 11, 2009.
Summons to Attend Oral Hearing from EPO Application No. 05852038.8, dated May 7, 2010.
Communication EPO Application No. 05852038.8, dated Sep. 6, 2010.
Communication Pursuant to Article 94(3) EPC from EPO Application No. 05852038.8, dated Sep. 10, 2010.
Invitation to Respond to Written Opinion from Singapore Patent Application No. 200703649-4, dated Sep. 17, 2008.
Examination Report from Singapore Patent Application No. 200703649-4, dated May 19, 2009.
Examination Report from New Zealand Patent Application No. 555248, dated Oct. 8, 2008.
Examination Report from New Zealand Patent Application No. 555248, dated Nov. 25, 2009.
Examination Report from New Zealand Patent Application No. 555248, dated Dec. 7, 2009.
Examination Report from New Zealand Patent Application No. 555248, dated Jun. 2, 2010.
Examination Report from New Zealand Patent Application No. 555248, dated Jun. 10, 2010.
Office Action from Chinese Patent Application No. 200580047054.2, dated Jul. 7, 2010 with unverified English Translation.
Bellows, The Use of siRNA Screening for the Development of Novel Therapies and Mapping of Genetic Pathways, MMG 445 Basic Biotechnology eJournal 2007 3:67-72.
Denning et al., High Throughput RNAi by Reverse Transfection With Low siRNA Concentrations, Qiagen GmbH, from ePoster The Online Journal of Scientific Posters, received at the EPO on Mar. 31, 2010.
SABiosciences (Annex 2), http://sabioscience.com/RNAiInfo.iph?pcatn=SIH1715685ABCD, printed Aug. 27, 2010.
Ming-Hon Hou et al., Effects of Polyamines on the Thermal Stability and Formation Kinetics of DNA Duplexes with Abnormal Structure, Nucleic Acids Research, 2001 vol. 29, No. 24 5121-5128.
Chan Yong Lee et al, Inhibitory Effect of Spermine of the Susceptibility of FNA for RNase A, Journal of the Korean Chemical Society, vol. 29, No. 6, 1985.
Super Array Bioscience's siRNA Array Plates and SureSilencing siRNA and Antibody Kits, and Antibody Kits, and Ambion's Silencer Phosphodiesterase siRNA Library, Mar. 19, 2004 from http://www.genomeweb.com/rnai/superarry-biosciences-s-sirna-arr.
SABiosciences, SureSilencing siRNA Arrays, dated Jan. 1, 2009, from http://www.sabiosciences.com/RNAiAnayPlate.phr.
SABiosciences, User Manual SureSilencing siRNA Arrays, Pathway-Focused Validated Gene Knockdown by RNA Interferance, Part #1029A, Version 1.1, Jan. 25, 2008.
Erfle, et al., "Reverse Transfection on Cell Arrays for High Content Screening Microscopy," Nature Protocols, vol. 2, No. 2, 2007.

* cited by examiner

METHOD OF DETERMINING A CELLULAR RESPONSE TO A BIOLOGICAL AGENT

CROSS-REFERENCE TO RELATED APPLICATIONS

This United States Patent Application claims benefit of U.S. Provisional Application Ser. No. 60/630,320, filed Nov. 22, 2004, and U.S. Provisional Application Ser. No. 60/678,165, filed May 04, 2005, both of which are incorporated herein by reference.

This United States patent application also cross-references the following United States patent applications filed herewith: U.S. patent application Ser. No. 11/283,484 filed 18 Nov. 2005, entitled APPARATUS AND SYSTEM HAVING DRY GENE SILENCING COMPOSITIONS, with Barbara Robertson, Ph.D., et al. as inventors; U.S. patent application Ser. No. 11/283,482 filed 18 Nov. 2005, entitled APPARATUS AND SYSTEM HAVING DRY GENE SILENCING POOLS, with Barbara Robertson, Ph.D., et al as inventors; and U.S. patent application Ser. No. 11/283,483 filed 18 Nov. 2005, entitled APPARATUS AND SYSTEM HAVING DRY CONTROL GENE SILENCING COMPOSITIONS, with Barbara Robertson, Ph.D., et al. as inventors, each of which is incorporated herein by reference.

BACKGROUND OF THE INVENTION

1. The Field of the Invention

The present invention relates to a system and method for studying a biological agent. More particularly, the present invention relates to a system and method that uses gene silencing for determining a cellular response to the biological agent.

2. The Related Technology

Recently, a natural cellular regulatory pathway was discovered that uses transcribed microRNA ("miRNA") in order to control protein production. The miRNA includes a duplex region of sense and antisense RNA. This regulatory pathway uses miRNA in order to target complementary mRNA to inhibit production of the encoded protein. Accordingly, a complex series of proteins are involved in this RNA interfering pathway to inhibit or stop production of the proteins encoded by the mRNA. As such, the process is referred to as RNA interference or RNAi.

Additionally, it has been found that the RNAi pathway can be used with synthetic dsRNA (e.g., siRNA) for silencing genes and inhibiting protein expression. This can allow for siRNA having specific sequences to be produced to target complementary DNA and/or mRNA encoding a specific protein. The siRNA can interact with the natural RNAi pathway to silence a target gene and inhibit production of the encoded polypeptide. The ability to silence a specific gene and inhibit production of the encoded protein has been used for basic research of gene function and cellular pathway analysis.

In order to induce gene silencing, the siRNA needs to be introduced into a cell. While the most common procedures for introducing nucleic acids into cells has been forward transfection, reverse transfection ("RTF") has been developed more recently and used as an alternative to forward transfection procedures. In certain versions of RTF protocols, a complex of lipid-nucleic acid (e.g., lipoplex) can be prepared and introduced into the test wells of a well plate. Cells are introduced into the test wells with the lipid-nucleic acid complexes, and incubated so that the siRNA can enter the cells. Examples of some RTF protocols can be found in U.S. Pat. No. 5,811,274 to Palsson, U.S. Pat. No. 5,804,431 to Palsson and U.S. Pat. No. 6,544,790 to Sabatini and in U.S. Published Applications 2002/0006664 to Sabatini and 2003/070642 to Caldwell et al. As described in these references, RTF procedures for nucleic acids generally can have fewer steps compared to traditional forward transfection and may offer benefits in attempting to isolate the transfected cells to particular regions of a single surface, such as a glass slide. However, RTF procedures for siRNA have not been optimized to the point of practical application, and improvements in gene silencing efficacy are still needed, especially for situations in which one is experimenting with multiple different siRNAs, different gene targets or different cell lines.

Cellular pathways have also been studied with regard to interactions with biological agents. As such, screening techniques have been used to study the interaction between biological agents and cells. These screening techniques can be used to identify which biological agents, such as drugs, have an effect on a particular cell, or interact with a polypeptide or protein produced by the cell. Additionally, screening techniques can be used with infectious biological agents to identify cell types that may or may not be susceptible to an infection, as well as identify drugs that can treat or prevent such infections. Thus, screening techniques can provide a wide array of valuable information that can be used for treating and/or preventing diseases. However, new screening techniques for studying biological agents continue to be developed in order to test various physiological responses.

Therefore, it would be advantageous to have an RTF protocol that can be used to determine the effect of biological agents on cells in the presence of gene silencing. Additionally, it would be beneficial to develop a method to use gene silencing in order to identify genes that encode for gene products that interact with biological agents, such as physiologically active agents or infectious agents.

BRIEF SUMMARY OF THE INVENTION

Generally, embodiments of the present invention include well plates, kits, systems, and methods of using the same for determining the effect of a biological agent on cells, which can include the biological agent being introduced into cells in the presence of gene silencing. Additionally, the well plates, kits, and systems include siRNAs that are configured to be implemented in an RTF format with biological agents in order to determine whether or not a silenced target gene is involved in a cellular response to the biological agent.

Accordingly, the method can include adding an aqueous medium to a first test well in a well plate that has a substantially dry gene silencing composition. The gene silencing composition can have at least a first siRNA which silences at least a first target gene. Also, the gene silencing composition can be configured such that the first siRNA is capable of being solubilized or suspended in the aqueous medium in an amount sufficient for transfecting cells in the first test well.

After the siRNA has been solubilized or suspended in the aqueous medium, cells are added to the first test well under conditions that permit transfection. Additionally, cells are added to a first control well. Any control well can include control siRNA or it can be devoid or substantially devoid of having siRNA. Also, the cells can be added to the wells under conditions that permit the siRNA to be introduced into the cell. The cells can be added in an amount of about $1 \times 10^3$ to about $3.5 \times 10^4$ per about 0.3 cm$^2$ to about 0.35 cm$^2$ of cell growth surface area. Any mode of transfection can be used to introduce the siRNA into the cells. Subsequently, the cells can be maintained in the test well and the control well for any appropriate duration before a biological agent is added to the well. This can include maintaining the test well and test control well under conditions so that cell growth, cell division, transfection and/or gene silencing occurs.

In one embodiment, a biological agent is added to the test and control wells after the cells are plated and/or after any gene silencing has occurred. In some instances the biological agent can be added to a well before the cells are added. Subsequently, the cells in the test well and control well can be maintained or incubated with the biological agent for a period of time sufficient for the biological agent to have an effect on normal cells in normal conditions. That is, the duration the biological agent is incubated with the cell cultures is a time sufficient for the effect of the biological agent to be observed in cells that have not been otherwise treated with siRNA.

In one embodiment, a determination can be made as to whether or not a first response to the biological agent by the cells in the first well is different from a first control response to the biological agent by the cells in the first control well. In the instance the test response is different from the first control response, the siRNA may silence a gene that is involved in a cellular response to the biological agent. Also, when the test response is different from the first control response it can be an indication that the target gene that was silenced is involved in the response by the cell to the biological agent. In the alternative, when the test response is substantially the same as the first control response, the first target gene may not be involved in a response by the cell to the biological agent.

In one embodiment, the method of studying a response by a cell to a biological agent can include adding cells to a second control well. The second control well can be a well that does not receive the biological agent, and can include control siRNA or it can be devoid or substantially devoid of having any siRNA. The second control well can be cultured and maintained in a manner similar to the test well and the first control well so that meaningful comparative data can be obtained. After being maintained in a manner substantially similar with the test well and/or first control well a determination can be made as to whether the first response to the biological agent by the cells in the first test well is different from a second control response to the absence of the biological agent by the cells in the second control well. In the instance the first test response is different from the second control response the target gene may be involved in the response by the cell to the biological agent. In the instance the first test response is substantially the same as the second control response the target gene may not be involved in the response by the cell to the biological agent. Additionally, the first control response in the first control well can be compared to the second control response in the second control well, which can provide data regarding the efficacy of the testing procedure. Alternatively, a control well that does not receive a biological agent, such as the second control well, can be used in a comparison with the test well in place of the first control well.

These and other embodiments and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention can be rendered by reference to specific embodiments thereof which are illustrated in the appended drawings. It is appreciated that these drawings depict only typical embodiments of the invention and are therefore not to be considered limiting of its scope. The invention can be described and explained with additional specificity and detail through the use of the accompanying drawings.

DETAILED DESCRIPTION OF THE PREFERRED EMBODIMENTS

Figure 1A:
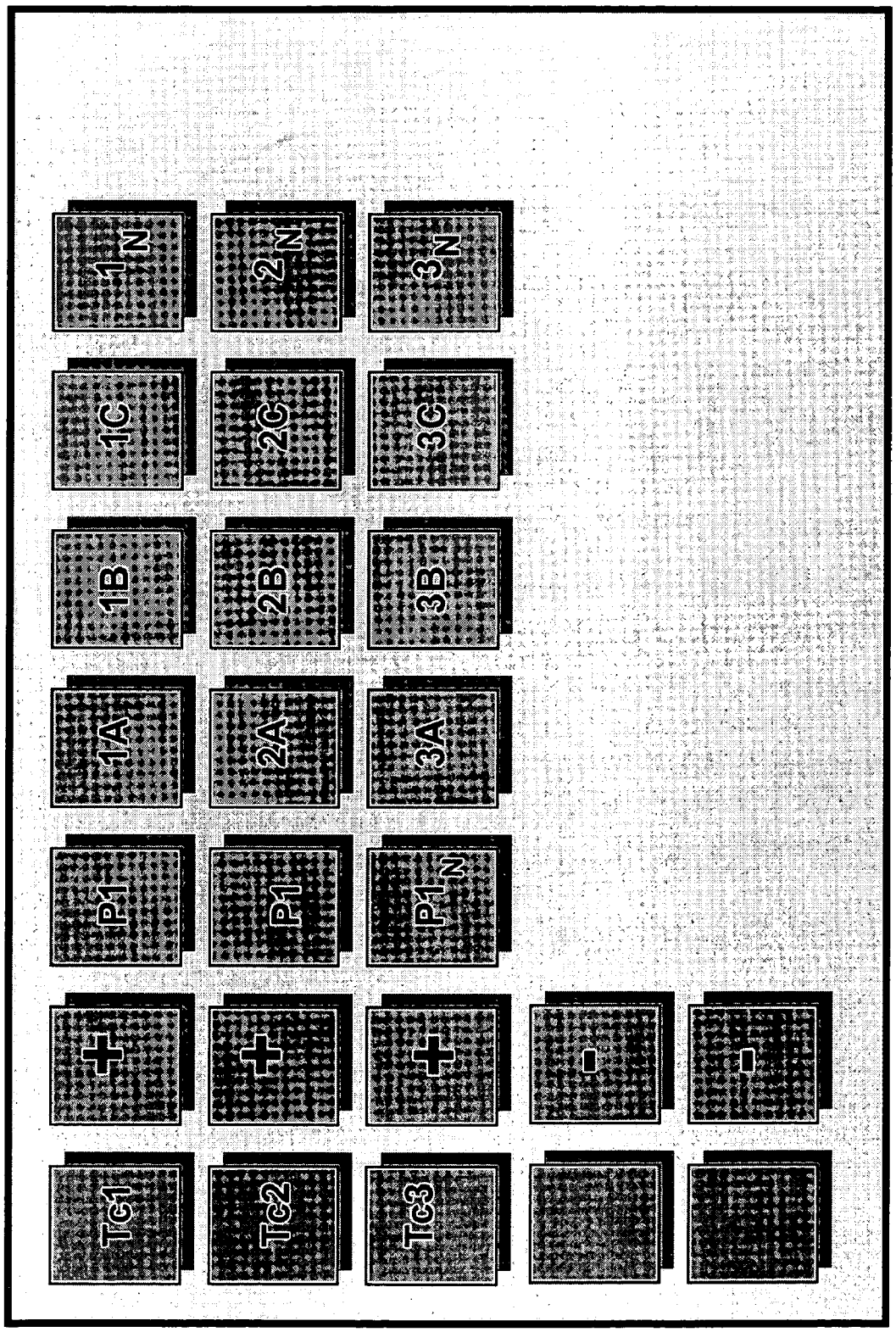
FIGS. 1A-1E are schematic diagrams that illustrate different embodiments of siRNA arrangements on a multi-well plate that can be used to study a biological agent.

Generally, the present invention is related to an apparatus and system for use in effecting gene silencing in cells in the presence of a biological agent. The apparatus includes plates with wells that have dry gene silencing compositions comprised of at least a first siRNA, which can be solubilized or suspended in an aqueous medium for use in RTF protocols. The siRNA can be configured for silencing cellular genomic or transgenes. In the instance the biological agent is a microorganism the genomic or transgenes within the microorganism can be silenced in order to assess any changes in the cellular response. The systems, which can be provided as kits, can include the plates, biological agent, polynucleotide carriers, polynucleotide carrier solutions, an aqueous medium, and the like.

The well plates, systems, kits, and methods of the present invention can be configured for use in high content screening ("HCS") or high throughput screening ("HTS") of biological agents with or without the use of laboratory automation equipment. Also, the well plates, systems, kits, and methods can also be used with automated systems, such as robotic systems. However, the well plates, systems, kits, and methods can also be used in RTF protocols without the aid of automated delivery systems, or robotics, and thus can provide an efficient alternative to costly robotic delivery systems for laboratories using manual processing. Thus, the well plates, systems, kits, and methods provide versatility in choice such that high throughput screening of biological agents can be done in a cost effective manner.

Additionally, the present invention can be used to screen for the contribution of a large number of genes to a cellular response to a biological agent. This can be used to screen the entire genome to identify the gene or combination of genes that encode for products that are involved in the cellular response or cellular event that is induced by the biological agent. Alternatively, the genes of a microorganism can be silenced to assess the effect on infection, replication, and release from a cell. These screening techniques can be employed along with HCS equipment and/or bioinformatics software in order to identify key genes, families of genes, biological pathways, and/or biological processes that are related to the cellular response to the biological agent, whether an active agent or a microorganism.

The following terminology is defined herein to clarify the terms used in describing embodiments of the present invention and is not intended to be limiting. As such, the following terminology is provided to supplement the understanding of such terms by one of ordinary skill in the relevant art.

As used herein, the term "antisense strand" is meant to refer to a polynucleotide or region of a polynucleotide that is at least substantially (e.g., 80% or more) or 100% complementary to a target nucleic acid of interest. Also, the antisense strand of a dsRNA is complementary to its sense strand. An antisense strand may be comprised of a polynucleotide region that is RNA, DNA, or chimeric RNA/DNA. Additionally, any nucleotide within an antisense strand can be modified by including substituents coupled thereto, such as in a 2' modification. The antisense strand can be modified with a diverse group of small molecules and/or conjugates. For example, an antisense strand may be complementary, in whole or in part, to a molecule of messenger RNA ("mRNA"), an RNA sequence that is not mRNA such as non-coding RNA (e.g., tRNA, rRNA, and the like), or a sequence of DNA that is either coding or non-coding. The antisense strand includes the antisense region of polynucleotides that are formed from two separate strands, as well as unimolecular siRNAs that are capable of forming hairpin structures with complementary base pairs. The terms "antisense strand" and "antisense region" are intended to be equivalent and are used interchangeably.

As used herein, the term "active agent" is meant to refer to a molecule or combination of molecules that have some activity or cause an effect on a cell or cellular process. Such activities or effects can be either beneficial or detrimental to the viability of a cell. Examples of active agents include chemicals, toxic chemicals, known drugs, potential drugs, nutraceuticals, vitamins, polypeptides, proteins, hormones, cytokines, enzymes, and the like.

As used herein, the term "biological agent" is meant to refer to a chemical or pathogen that can be introduced into a cell. The biological agent can have a property that induces a physiological response in a subject such as a plant or an animal (e.g., humans, mice, rats, and the like) or a plant. Preferably, the biological agent can induce a cellular response when introduced into a cell. Biological agents can be molecules or combinations of molecules that can be produced by natural processes or chemical reactions. Additionally, biological agents can be microorganisms that are capable of being produced by replication.

As used herein, the terms "dried" or "dry" as used in connection with gene silencing compositions are meant to refer to a composition that is not fluidic and does not flow. However, this does not exclude small amounts of water or other solvents, and includes amounts of water remaining in an RNA preparation that has equilibrated at standard or ambient conditions. For example, at one atmosphere of pressure, room temperature, and ambient humidity, such that the preparation is not in a substantially liquid form but instead is "dried" in the well. An siRNA preparation is "dried" or substantially "dry" if, at about one atmosphere pressure, at about 20 to 40° C., and at about 50 to about 95% humidity, the preparation is equilibrated and, when the well plate is inverted or tilted to, for example, 90° from horizontal, the RNA preparation does not displace or flow within the well. This is in comparison to a liquid preparation which would flow or run when tilted. In various embodiments, methods for using the dry gene silencing composition in order to perform a transfection can include solubilizing or suspending the dried preparation in a suitable aqueous medium to form a mixture. Additionally, the suitable aqueous medium can include a polynucleotide carrier capable of facilitating introduction of the siRNA into a cell, and exposing the mixture to one or more cells to achieve transfection.

As used herein, the term "gene silencing" is meant to refer to a process by which the expression of a specific gene product is inhibited by being lessened, attenuated, and/or terminated. Gene silencing can take place by a variety of pathways. In one instance, gene silencing can refer to a decrease in gene product expression that results from the RNAi pathway, wherein an siRNA acts in concert with host proteins (e.g., RISC) to degrade mRNA in a sequence-dependent manner. Alternatively, gene silencing can refer to a decrease in gene product expression that results from siRNA mediated translation inhibition. In still another alternative, gene silencing can refer to a decrease in gene product expression that results from siRNA mediated transcription inhibition. The level of gene silencing can be measured by a variety of methods, which can include measurement of transcript levels by Northern Blot Analysis, B-DNA techniques, transcription-sensitive reporter constructs, expression profiling (e.g., DNA chips), and related technologies and assays. Alternatively, the level of gene silencing can be measured by assessing the level of the protein encoded by a specific gene that is translated from the corresponding mRNA. This can be accomplished by performing a number of studies including Western Blot analysis, measuring the levels of expression of a reporter protein, such as colorimetric or fluorescent properties (e.g., GFP), enzymatic activity (e.g., alkaline phosphatases), or other well known analytical procedures.

As used herein, the term "microorganism" is meant to refer to a microscopic organism that can be characterized as being alive or capable of replication. Accordingly, microorganisms can be either benign or pathogenic. Examples of pathologic microorganisms include viruses, bacteria, fungi, protozoa, and the like.

As used herein, the term "polynucleotide" is meant to refer to polymers of nucleotides linked together through internucleotide linkages. Also, a polynucleotide includes DNA, RNA, DNA/RNA, hybrids including polynucleotide chains of regularly and/or irregularly alternating deoxyribosyl moieties and ribosyl moieties (i.e., wherein alternate nucleotide units have an —OH, then and —H, then an —OH, then an —H, and so on at the 2' position of a sugar moiety), and modifications of these kinds of polynucleotides. Also, polynucleotides include nucleotides with various modifications or having attachments of various entities or moieties to the nucleotide units at any position.

As used herein, the terms "rational design" and "rationally designed" are meant to refer to the selection or design of one or more siRNA(s) for use in a gene silencing application based upon one or more criteria that are independent of the target sequence. As such, rationally designed siRNA are selected to specifically interact with and inhibit polypeptide translation from a selected mRNA. Thus, for any one target mRNA there may be hundreds of potential siRNA of 18-31 base pairs that are 100% complementary to the target mRNA. In part, this is because a single mRNA may have multiple sequences that can be specifically targeted by the siRNA. However, it is likely that not all of the siRNA will have equal functionality. Through empirical studies, a number of other factors including the presence or absence of certain nitrogenous bases at certain positions, the relative GC content, and the like, can affect the functionality of particular siRNA. Additional information regarding rationally designed siRNA can be found in commonly owned U.S. patent application Ser. No. 10/714,333, filed on Nov. 14, 2003, related PCT application PCT/US/03/36787, published on Jun. 3, 2004 as WO 2004/045543 A2, U.S. patent application Ser. No. 10/940,892, filed on Sep. 14, 2004, published as U.S. Patent Application Publication 2005/0255487, related PCT application PCT/US/04/14885, filed May 12, 2004, and U.S. Patent Application Publication 2005/0246794, wherein each is incorporated herein by reference.

As used herein, the term "reverse transfection" and abbreviation "RTF" are each meant to refer to a process for introducing nucleic acid, such as an siRNA, into a cell. Such an introduction of an siRNA into a cell can be accomplished by combining the nucleic acid and cell in a well, wherein the cell has not yet been previously adhered or maintained on the growth surface. The reverse transfection proceeds by contacting the nucleic acid onto a cellular surface in a manner such that the nucleic acid can enter into the cell. Usually, the siRNA is complexed with a lipid or other polynucleotide carrier prior to being contacted to the cells; however, other modes of transfection can be used to introduce the siRNA into the cell. Reverse transfection differs from forward transfection because the cells have not been seeded and maintained on the cellular growth surface of a well or other container before addition of the siRNA.

As used herein, the term "sense strand" is meant to refer to a polynucleotide or region that has the same nucleotide sequence, in whole or in part, as a target nucleic acid such as a messenger RNA or a sequence of DNA. The term "sense strand" includes the sense region of a polynucleotide that forms a duplex with an antisense region of another polynucleotide. Also, a sense strand can be a first polynucleotide sequence that forms a duplex with a second polynucleotide sequence on the same unimolecular polynucleotide that includes both the first and second polynucleotide sequences. As such, a sense strand can include one portion of a unimolecular siRNA that is capable of forming hairpin structure, such as an shRNA. When a sequence is provided, by convention, unless otherwise indicated, it is the sense strand or region, and the presence of the complementary antisense strand or region is implicit. The phrases "sense strand" and "sense region" are intended to be equivalent and are used interchangeably.

As used herein, the term "siRNA" is meant to refer to a small inhibitory RNA duplex that induces gene silencing by operating within the RNA interference ("RNAi") pathway. These siRNA are dsRNA that can vary in length, and can contain varying degrees of complementarity between the antisense and sense strands, and between the antisense strand and the target sequence. Each siRNA can include between 17 and 31 base pairs, more preferably between 18 and 26 base pairs, and most preferably 19 and 21 base pairs. Some, but not all, siRNA have unpaired overhanging nucleotides on the 5' and/or 3' end of the sense strand and/or the antisense strand. Additionally, the term "siRNA" includes duplexes of two separate strands, as well as single strands that can form hairpin structures comprising a duplex region, which may be referred to as short hairpin RNA ("shRNA").

As used herein, the terms "siRNA library" or "RTF siRNA library" is meant to refer to an array of siRNAs for use in analyzing a particular biological pathway or gene target. An siRNA library comprises various siRNA pool reagents for analyzing a particular pathway or gene target. A pool typically comprises two or more non-identical siRNA directed against a single target gene. Usually, a pool includes four or more non-identical siRNA that are rationally designed. An exemplary list of siRNA libraries is provided in Table 1 below. Sequences used in certain siRNA libraries, including pool reagents, are provided in Table I and Table II of the incorporated provisional application.

As used herein, the terms "siRNA pool," "pool," "pool of siRNAs," and "pool reagents" are meant to refer to two or more siRNA, typically four siRNA, directed against a single target gene, mRNA, and/or translation of a protein. The siRNA of the pool reagent can be rationally designed by being selected according to non-target specific criteria. For example, two nanomoles of each pool reagent can be sufficient for transfecting cells in about 200 wells of multiple 96-well plates, using 100 nM siRNA concentration. Pool reagents can be plated as a pool (i.e., the two or more siRNA of Dharmacon's SMARTpool® Reagent in a single transfection well). The individual siRNAs that comprise the SMARTpool® Reagent, sometimes referred to herein as SMARTselection® siRNA (Dharmacon, Inc.), can also be plated individually A on the same plate as the SMARTpool™ Reagent.

As used herein, the term "target" is used in a variety of different forms throughout this document and is defined by the context in which it is used. The term "target gene" is meant to refer to the gene that encodes the protein to be silenced by the siRNA, and encodes for the production of the target mRNA. The term "target mRNA" is meant to refer to an mRNA against which a given siRNA is direct to silence the transcription of the polypeptide product. The term "target sequence" and "target site" are meant to refer to a sequence within the mRNA, miRNA, or DNA coding or promoter region to which the sense strand of an siRNA exhibits varying degrees of homology and the antisense strand exhibits varying degrees of complementarity. The term "target polypeptide" or "target protein" is meant to refer to the gene product encoded by the target gene, target mRNA, and/or target sequence. The term "siRNA target" can refer to the gene, mRNA, or protein against which the siRNA is directed to for silencing. Similarly, "target silencing" can refer to the state of silencing a gene, or the corresponding mRNA or protein.

As used herein, the term "transfection" is meant to refer to a process by which nucleic acids are introduced into a cell. The list of nucleic acids that can be transfected is large and includes, but is not limited to, siRNA, shRNA, sense and/or anti-sense sequences, DNA, RNA, and the like. There are multiple modes for transfecting nucleic acids into a cell including, but not limited to, electroporation, calcium phosphate delivery, DEAE-dextran delivery, lipid delivery, polymer delivery, molecular conjugate delivery (e.g., polylysine-DNA or -RNA conjugates, antibody-polypeptide conjugates, antibody-polymer conjugates, cholesterol conjugates, or peptide conjugates), microinjection, laser- or light-assisted microinjection such as, for example, optoporation or photoporation with visible and/or nonvisible wavelengths of electromagnetic radiation, and the like. Transfections can be "forward transfections" whereby cells are first plated in wells and then treated with a nucleic acid or they can be "reverse transfections" (RTF) whereby the nucleic acid is combined with the cells before or during being plated and/or attached to the bottom of the well. Any mode of transfecting cells, such as those described above, can be used with the present invention by inducing the nucleic acid to be introduced into a cell after the siRNA is solubilized or suspended in the aqueous medium to implement reverse transfection. Details regarding a mode of reverse transfection are described in more detail below.

As used herein, the term "nucleotide" is meant to refer to a ribonucleotide, a deoxyribonucleotide, or modified form thereof, as well as an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs. Nucleotides are well known in the art. Nucleotide analogs include nucleotides having modifications in the chemical structure of the base, sugar and/or phosphate, including, but not limited to, 5'-position pyrimidine modifications, 8'-position purine modifications, modifications at cytosine exocyclic amines, substitution of 5-bromo-uracil, and 2'-position sugar modifications (e.g., 2' modifications). Such modifications include sugar-modified ribonucleotides in which the 2'-OH is replaced by a group such as an H, OR, R, halo, SH, SR, $NH_2$, NHR, $NR_2$, or CN, wherein R is an alkyl or aliphatic moiety. Nucleotide analogs are also meant to include nucleotides with bases such as inosine, queuosine, xanthine, sugars such as 2'-methyl ribose, non-natural phosphodiester linkages such as methylphosphonates, phosphorothioates, and peptides. Also, reference to a first nucleotide or nucleotide at a first position refers to the nucleotide at the 5'-most position of a duplex region, and the second nucleotide is the next nucleotide toward the 3' end. In instances the duplex region extends to the end of the siRNA, the 5' terminal nucleotide can be the first nucleotide.

The use of units to define measurable quantities of material, such as concentration, weight, and volume, are intended to be those that are routinely employed by those of skill in the art. Additionally, the units are preferably interpreted to correspond with the metric system. Also, the use of "u," as in "ug" or "uL" is meant to refer to "micro" as applied to microgram and microliter, respectively.

Additionally, while the foregoing term definitions are intended to supplement the knowledge of one of ordinary skill in the art, not every term within this document has been defined. As such, the undefined terms are intended to be construed with the knowledge of one of ordinary skill in the art and/or the plain meaning of the term. Additionally, the foregoing terms are not intended to be limited by the examples provided therein, but are intended to be useful in understanding and practicing the invention as described herein.

I. Reverse Transfection

Generally, the present invention provides well plates, systems, kits, and methods for implementing reverse transfection ("RTF") of siRNAs. As such, the RTF protocol can be implemented to silence a selected gene or combination of genes to study the ability of a gene product to interact with or be associated with a cellular response to a biological agent, wherein the biological agent can be an active agent or a microorganism. Additionally, the RTF protocol can be used to assess genes involved in an infectious pathway. This can be done by using gene silencing to study genes in the cell that respond to the pathogenic infection or silencing genes in the pathogen.

In one embodiment, the present invention includes an RTF protocol for introducing siRNA into a cell to study the effect of gene silencing on a biological agent that is also added to the cell. Such a method can include providing a well plate that includes a first test well having a substantially dry gene silencing composition. The gene silencing composition can include at least a first siRNA which silences at least a first target gene so that the production of the corresponding gene product is inhibited or stopped. Also, the gene silencing composition can include a pool of siRNAs which silences the target gene.

The siRNA is present in the first test well as part of the dry gene silencing composition so that the plates can be prepared, sealed, stored, and/or shipped long before an RTF protocol is performed. In part, this is because the dry gene silencing composition can stably retain the siRNA in a functional condition within the well, and be suspended or solubilized with an aqueous medium during the RTF protocol. Thus, a well plate having the gene silencing composition can be manufactured and hermetically sealed in an inert environment within a sterile container, wherein the plate can include different wells with predefined types of siRNA for specific gene targets, which can include an individual siRNA and pools of siRNAs. Such types of siRNA and intended gene targets for silencing are described in more detail below.

An aqueous medium can be added to the test well that contains the gene silencing composition to suspend or solubilize the siRNA into the aqueous medium. The aqueous medium is allowed to solubilize or suspend the siRNA for a sufficient duration so that most or all of the siRNA is in the aqueous medium.

After the siRNA is adequately solubilized or suspended, cells are added to the test well under conditions that permit the siRNA to be introduced into the cells. The cells are usually added in an amount of about $1 \times 10^3$ to about $3.5 \times 10^4$ cells per about $0.3$ cm$^2$ to about $0.35$ cm$^2$ of cell growth surface area. The conditions that promote an siRNA entering a cell can be described by typical cell culture techniques used for plating cells that are well known in the art. That is, the cells can be added to the well that contains the siRNA in a manner similar to ordinary plating. Additionally, any mode of transfection can be used to introduce the siRNA into the cells. The test well containing the siRNA and cells can be incubated for a sufficient duration for gene silencing to occur, which is typically less than 72 hours, more preferably less than 48 hours, and most preferably about 24 hours or less. Alternatively, the aqueous medium that comprises the cells can be used to solubilize or suspend the siRNA with the cells.

In one embodiment, the RTF protocol can include adding a polynucleotide carrier to the test well to form an siRNA-carrier complex, wherein the siRNA-carrier complex is suspended or solubilized in the aqueous medium. After the cells are added, the siRNA-carrier complex can contact the cell surface to induce endocytosis of the complex. The polynucleotide carrier can be added as part of the aqueous medium or in addition thereto. Thus, the polynucleotide carrier can be presented in an aqueous medium as either solubilized or suspended therein. The polynucleotide carrier can be a cationic lipid, polymer, lipopolymer, and the like. Alternatively, the siRNA can include a conjugate, such as a cholesterol or polypeptide, which can enhance passive delivery of the siRNA into the cells, and thus eliminate the need for polynucleotide carrier; however, such passive delivery conjugates can be advantageously used with polynucleotide carriers.

After the cells are combined with the siRNA, the well plate can be maintained under conditions so that cell growth, cell division, transfection, and/or gene silencing occurs. Usually, the cells are maintained in the presence of the siRNA for about 6 to about 72 hours to effect gene silencing, more preferably about 12 to about 48 hours, even more preferably from about 18 hours to about 36 hours, and most preferably about 24. However, it should be recognized that the cells are incubated with the siRNA for a time period sufficient for silencing a gene so that the amount of corresponding gene product decreases. As such, the production of a target polypeptide can be silenced by at least 50%, more preferably by at least 70%, even more preferably by at least 80%, and most preferably by at least 90%.

In instances where cells that grow in suspension contain the target, such cells can be added to the wells at an appropriate cell density and plates can be spun under low gravity forces that are not detrimental to cell viability to bring the cells and lipids into close proximity on the bottom of the well.

In one embodiment, cells can be added to a first control well. The first control well can include control siRNA or it can be devoid or substantially devoid of having any siRNA. Subsequently, the cells can be maintained in the control well for any appropriate duration before a biological agent is added to the well. This can include maintaining the control well under conditions so that cell growth, cell division, transfection, and/or gene silencing occurs.

In one embodiment, a biological agent is added to the cells in the test well and the cells in the first control well. In different studies, it can be appropriate for the biological agent to be added to the wells before, during, or after the cells are added to the wells. Additionally, the biological agent can be added to the wells before or after gene silencing occurs in the test well. The biological agent is typically added from about 0.25 to about 72 hours after the cells are added to the wells, more preferably from about 1 hours to about 48 hours, even more preferably from about 6 hours to about 36 hours, and most preferably from about 12 to about 24 hours after the cells are added to the wells. Subsequently, the cells in the test well and first control well can be maintained or incubated with the biological agent for a period of time sufficient for the biological agent to have an effect on normal cells in normal conditions. That is, the duration the biological agent is incubated with the cell cultures is a time sufficient for the effect of the biological agent to be observed in cells that have not been otherwise treated with any test reagent such as siRNA.

Subsequently, the cells in the test well and first control well can be assayed for a response to the biological agent. The response to the biological agent can be detected by any protocol that measures a cellular response to the biological agent, or directly measures the presence of the biological agent in the cells. The cellular response can be detected by methods described herein or well-known methods in the art, which can include toxicity studies and protein analysis. This can also include photometric analyses that direct light through the wells, wherein it can be favorable for the test well and first control well to each have a substantially flat well floor comprised of a translucent or transparent material such as polystyrene.

In one embodiment, a determination can be made as to whether or not a first response to the biological agent by the cells in the test well is different from a first control response to the biological agent by the cells in the first control well. In the instance the first response is different from the first control response the first siRNA may silence a gene that is involved in a cellular response to the biological agent. Also, the first response being different from the first control response may be linked to a biological pathway related to the biological agent being compromised. In any event, when the first response is different from the first control response it can be an indication that the first target gene is involved in the response by the cell to the biological agent. In the alternative, when the first response is substantially the same as the first control response, the first target gene may not be involved in a response by the cell to the biological agent.

In one embodiment, the method of studying a response by a cell to a biological agent can include adding cells to a second control well. The second control well can be a well that does not receive the biological agent, and can be used in addition to or in place of the first control well that does receive the biological agent. The second control well can be cultured and maintained as the test well and the first control well so that meaningful comparative data can be obtained. The second control well can include control siRNA or it can be devoid or substantially devoid of having any siRNA. After being maintained in a manner substantially similar with the first well and/or first control well, a determination can be made as to whether or not the first response by the cells in the test well to the biological agent is different from a second control response by the cells in the second control well in the absence of the biological agent. In the instance the first response is different from the second control response the first target gene may be involved in the response by the cell to the biological agent. In the instance the first response is substantially the same as the second control response the first target gene may not be involved in the response of the cell to the biological agent. Additionally, the first control response can be compared to the second control response when both are used, which can provide data regarding the efficacy of the testing procedure.

In one embodiment, the cells in the test well and first control well can contain the target gene. As such, the target gene can be a genomic gene in the cells. Also, the target gene can be a plasmid that has been transfected into the cells. Alternatively, the target gene may be contained in the cells of the first well and first control well by being within a virus, fungi, bacteria, or other microbe that has entered the cell. This can include the target gene being a microbial genomic gene or a transgene.

In one embodiment, the present invention includes a method of determining a cellular response to a biological agent. This can include identifying a gene involved in a response by a cell to a biological agent. The study can be performed by adding an aqueous medium to a plurality of wells in a well plate. The plate can include at least a first set of wells that contain substantially dry gene silencing compositions. The gene silencing compositions can have at least a first siRNA which silences a first target gene. Also, the gene silencing composition can be configured such that the first siRNA is capable of being solubilized or suspended in the aqueous medium in an amount sufficient for transfecting cells in the well. Additionally, cells can be added to the first set of wells under conditions that permit transfection. Cells can also be added to a first set of control wells, wherein a well in the first set of control wells corresponds to a well in the first set of wells that contains a gene silencing composition. The cells, first siRNA, and first set of control wells can be selected to provide a biological comparison between the results obtained from the study. The cells in the first set of wells and in the first set of control well can be maintained for any duration before the biological agent is added to the first set of wells. The biological agent may or may not be added to the first set of control wells depending on the study. The cells can be incubated with the biological agent before a cellular response thereto is detected and/or measured. A determination can be made as to whether or not a first response to the biological agent by the cells in the first set of wells is different from a first control response obtained from the first set of control wells. In the instance the first response is different from the first control response it is an indication that the first target gene is involved in the response by the cell to the biological agent.

In one embodiment, the cells in the test well transfected with the siRNA in the RTF format can be assessed for cell viability, gene silencing, target protein production, and the like. Also, the cells in either the first control well or the second control well can be assessed for cell viability, gene silencing, protein production, and the like. The cell viability studies can be performed in the well plate in accordance with well known procedures. Additionally, the gene silencing and/or activity of the biological agent can also be assessed with the contents in the well by various techniques well known in the art to assess the presence or absence of target proteins. Alternatively, the amount of gene silencing and/or activity of the biological agent can be assessed by removing the contents from the well by well known assays. In various embodiments, the well is designed to be compatible with optical detection systems such as, for example, UV, luminescence, fluorescence, or light scattering detection systems. In embodiments compatible with optical detection systems, the walls of the well can be made opaque, or rendered, such that light scattering that can interfere with optical detection is reduced or minimized.

In one embodiment, the cellular response to the biological agent in the presence of gene silencing can be detected or monitored using systems for performing high content screening ("HCS") or high throughput screening ("HTS"). An HCS analysis can be used to measure specific translocation and morphology changes, receptor trafficking, cytotoxicity, cell mobility, cell spreading, and the like. HCS studies can be performed on an ArrayScan® HCS Reader, or a KineticScan® HCS Reader (Cellomics, Inc.) Additional information on HCS can be found in U.S. Pat. Nos. 6,902,883, 6,875,578, 6,759,206, 6,716,588, 6,671,624, 6,620,591, 6,573,039, 6,416,959, 5,989,835, wherein each is incorporated herein by reference. HTS analyses can be performed using a variety of available readers, typically of the fluorescence from each well as a single measurement.

In one embodiment, the invention includes a well plate configured for having the contents of a well transferred to a location, device, or system wherein detection of the results of an siRNA RTF protocol is carried out. As such, wet transfer detection systems can be employed that include systems wherein cells are transferred from wells to a substrate such as nitrocellulose. Following the transfer of the well contents to the substrate a detection protocol can be implemented. An example of such a well plate transfer system can include nitrocellulose, wherein the well contents can be treated such that cell membranes are permeabilized or disrupted so as to gain access to intracellular contents. The transfer of the well contents to the nitrocellulose can be achieved by any suitable method including gravity or use of a vacuum manifold. The nitrocellulose containing the well contents can then be further subjected to a detection protocol that uses antibody-based detection systems and the like to detect the presence level of one or more contents of the cells that comprise a particular well.

In one embodiment the number of cells in a test well or control well can be varied to optimize gene silencing and/or activity of the biological agent. It has been found that siRNA RTF protocols can have more favorable results with lower cell densities compared to RTF protocols using DNA. For example, 96-well plates can include cell densities of about 1,000-35,000 cells per well, more preferably about 2,000-30,000 cells per well, even more preferred are cell densities of about 2,500-20,000 cells per well, still more preferably about 3,000-15,000 cells per well, and most preferable are cell densities of about 3,500-10,000 cells per well. These cell densities can be favorable for studying biological agents in the presence of gene silencing. Also, the number of cells per well can be extrapolated to wells having different cell culture areas. One possible equation for calculating the appropriate number of cells that are placed in a given well is based on a 96-well plate having a cell culture area of about 0.3 cm² to about 0.35 cm², wherein well # 2 is the 96-well plate, and is described as follows:

$$\text{cells in well } \#1 = \left(\frac{\text{area of well } \#1}{\text{area of well } \#2}\right) \times \text{cells in well } \#2$$

In one embodiment, the present invention is directed to studying the effect of gene silencing on a cellular response to a biological agent. As such, the study protocols can include any of the following: (1) selecting the type of plate; (2) selecting an appropriate solution to deliver and dry the siRNAs in the wells; (3) selecting an individual siRNA or pool of siRNAs to silence specific genes; (4) identifying any modifications or conjugates that can be applied to the individual siRNA in order to enhance siRNA stability and/or specificity; (5) applying and drying the siRNAs on well floor so that it can be solubilized or suspended in an appropriate aqueous medium; (6) selecting an appropriate mode of transfection to introduce the siRNA into the cells; (7) solubilizing or suspending the siRNAs; (8) selecting an appropriate polynucleotide carrier and complexing the siRNA with the polynucleotide carrier to form an siRNA-carrier complex; (9) combining the siRNA-carrier complex with the cell type or types of choice; (10) selecting a biological agent to test; (11) selecting an amount of the biological agent to test; (12) determining when to administer the biological agent to the cells; and (13) administering the biological agent to the cells. Thus, siRNA RTF protocols can be used to test the effects of gene silencing on a cellular response to a biological agent.

II. Well Plates

In one embodiment, the present invention includes the use of gene silencing solutions dried in the bottom of a well in a well plate. The well plates used in connection with the present invention are preferably formatted and distinct well arrays (e.g., a 48, 96, 384, or 1536-well plate) that can be purchased from any number of commercial sources of cell culture plates and other cell culture surface-containing devices, including products such as NUNC™, NUNCLON™, MICROWELL™ and FLUORONUNC™ plates (e.g., each of which may be obtained from Nalge Nunc International of Rochester, N.Y., and Nunc A/S of Denmark), COSTAR™, COSTAR THERMOWELL™ and CORNING™ plates (e.g., each of which is available from Corning), BD FALCON™ and OPTILUX™ plates (e.g., available from Becton, Dickinson and Company) and GREINER™, CELL COAT™ and CELLSTAR™ plates (e.g., available from Greiner Bio-One).

In one embodiment, the well plate can be characterized by being configured to be suitable for cell growth and propagation. A well plate can be made of glass, polystyrene, other polymeric material or any equivalent materials, and can have rounded and/or flat well floors. However, certain analytical equipment can have enhanced functionality when using flat well floors. Additionally, wells having substantially flat floors can provide uniform cell spacing and monolayer formation. Thus, it can be preferable for the well floor to have a substantially flat bottom surface. The well floor can have a physical or chemical treatment, such as irradiation, corona discharge, plasma discharge, or microwave plasma discharge of polystyrene. Such treatments can be conventional in tissue culture surfaces upon which adherent eukaryotic cells may adhere and grow. Additionally, the wells may not be modified by any chemical coating, or they can be coated with poly-L-lysine ("PLL"), laminin, collagen, or equivalent substances that improve the adherence of cells.

Additionally, it can be preferable for each plate to have between 6 and 2000 wells, and more preferably having 1536 wells, 384 wells, or 96 wells. Also, it can be preferable for the wells to have a volume that varies between about 5 to about 2000 microliters ("uL"), and the total culture area, which is represented by the well bottom surface or cell floor, to range between about 0.02 cm² to about 4.2 cm², and about 0.3 cm² to about 0.35 cm² for a 96-well plate. Additional information regarding suitable well plates can be reviewed in the incorporated reference U.S. patent application Ser. No. 11/283, 484, entitled APPARATUS AND SYSTEM HAVING DRY GENE SILENCING COMPOSITIONS, with Barbara Robertson, Ph.D., et al. as inventors.

Furthermore, in some instances it can be preferably that the wells are not coated with materials such as MATRIGEL™ (Beckinson Dickerson), or are not manufactured with methods similar to those used to construct CELLBIND™ plates (Corning). In part, this is because both of these technologies are conventionally used to enhance cell attachment but have been found to reduce or diminish siRNA uptake and/or gene silencing in the RTF protocol.

III. Gene Silencing Plates

In one embodiment of the present invention, a well plate in accordance with the foregoing can be configured to be a gene silencing plate. Accordingly, the well plate can include a gene silencing composition in one or more wells. The well plates can be gene silencing plates by having an siRNA-containing solution applied to at least one well, which is then dried in a manner that removes the solution and leaves a dried gene silencing composition. The gene silencing composition can have at least one siRNA that silences at least a first target gene or a pool of siRNAs that silence the target gene. Also, the gene silencing composition can have a single siRNA directed against a family of related genes. Additionally, the well plate can have a well having multiple siRNAs targeting a single gene, or multiple siRNAs targeting multiple genes. The gene silencing plates can be prepared as described in the incorporated reference U.S. patent application Ser. No. 11/283,484, entitled APPARATUS AND SYSTEM HAVING DRY GENE SILENCING COMPOSITIONS, with Barbara Robertson, Ph.D., et al. as inventors.

Preferably, the siRNA delivered to a test well is present in a total amount that can provide a desired final concentration after being solubilized or suspended in the aqueous medium. It can be preferable that the final concentration of siRNA to effect gene silencing can be less than or equal to about 250 nM, more preferably less than or equal to 100 nM, even more preferably less than or equal to about 50 nM, still even more preferably less than or equal to about 25 nM, and most preferably less than or equal to about 10 nM. In some instances it the siRNA may be present at less than or equal to 1 nM. The amount of siRNA delivered to a well in a 96-well plate can be from 0.1 picomoles ("pm") to 100 pg, more preferably about 1 pm to about 75 pm, and most preferably about 10 pm to about 62.5 pm per well, where corresponding amounts of siRNA can be calculated for plates having other numbers of wells.

Additionally, the total amount of siRNA added to each well can be sufficient for use in a single RTF protocol within that well. That is, the siRNA in the gene silencing composition can be present in an amount to only be used with the cells added to the well. As such, the total amount of siRNA dried in the well can be insufficient for performing two RTF protocols in two different wells. This is because the total amount of siRNA provided in the gene silencing composition is configured for a single RTF protocol in order to produce optimal results. Also, this eliminates the need to make a stock siRNA solution that is transferred into multiple wells, thereby reducing the complexity of the RTF protocol and increasing efficacy.

The siRNA solution can be transferred to the well floor by any method of delivering liquids into wells of a well plate, which can be manual or automated. Various methods can be used to dry the siRNA solution into a gene silencing composition. In one embodiment, the plates are allowed to dry at room temperature in a sterile setting which allows the siRNA solution to evaporate leaving behind the pool of siRNAs. The dried plates can be sterile so that cells are not contaminated during the RTF protocol. Dried plates are preferably vacuum-sealed or sealed in sterile packages in the presence of inert gases, and stored at temperatures ranging from −80° C. to 37° C. for extended periods of time without loss of silencing functionality. Thus, the plates having the dry gene silencing compositions in at least one well can be stored at room temperature and shipped via traditional routes and still maintain the integrity and functionality of the siRNA.

In one embodiment, the well plate can have various wells that can be used for control and calibration functions. As such, the well plate can have at least one well devoid or substantially devoid of siRNA. Also, the well plate can have at least one well that includes at least a first control siRNA. For example, the control siRNA can include at least one of the following: (a) an siRNA that is capable of silencing a known gene; (b) transfection control siRNA; (c) an siRNA having a fluorescent marker; (d) siRNA having at least one toxic motif, (e) a non-functional siRNA; or (f) a siRNA that inhibits being taken in and processed by RISC.

IV. siRNA

In one embodiment, the foregoing dry gene silencing compositions include at least a first siRNA which silences at least a first target gene, and can include a pool of siRNAs. The gene silencing composition is configured such that the siRNA is capable of being solubilized or suspended in an aqueous medium in an amount sufficient for transfecting cells in the well. Optionally, the total amount of siRNAs in the well is sufficient for implementing reverse transfection only for that well. Additionally, it is optional for the siRNA to have at least one of a hairpin structure, modification or a conjugate. Also, the siRNA can be rationally designed to target the gene.

In one embodiment, the siRNA is selected to optimize functionality in silencing the target gene. Preferably, the siRNA has between 50% and 100% gene silencing functionality, more preferably between 70% and 100%, even more preferably between 80% and 100%, and most preferably a gene silencing functionality between 90% and 100%. The design of a functional siRNA can be based on providing modifications that increase target specificity, increase stability, are rationally designed for particular mRNA targets, and combinations thereof. In addition to targeting mRNA, any other RNA including non-coding RNA, siRNA can target a promoter region, the open reading frame, the 5' UTR, the 3' UTR, or other regions of DNA.

In one embodiment, it can be preferably to select siRNA from a list that have been identified from being rationally designed. As such, the siRNA can be selected from Table I and Table II of U.S. Provisional Application Ser. No. 60/678, 165. Table I is entitled "siGENOME Sequences for Human siRNA," and consists of columns "Gene Name," "Accession No.," "Sequence," and "SEQ. ID NO." Table I lists 92,448 19-mer siRNA sense strand sequences, where antisense strand sequences were omitted for clarity. The siRNA sequences listed in Table I includes SEQ. ID NOs. 1-92,448, wherein each preferably can also include a 3' UU overhang on the sense strand and/or on the antisense strand. Each of the 92,448 sequences of Table I, when used in an siRNA, can also comprise a 5' phosphate on the antisense strand. Of the 92,448 sequences listed in Table I, 19,559 have an on-targeting set of modifications. A list of sequences, identified by SEQ. ID NO., that have on-target modifications is presented in Table II, entitled "List of Table I Sequences Having On-Target Modifications Identified by SEQ. ID NO." On-target modifications are on SEQ. ID NOs. 1-22,300.

In one embodiment, an siRNA can be configured as an shRNA. This because an shRNA is a form of siRNA that includes a hairpin structure having a loop region connecting a sense region with an antisense region. Also, the shRNA can have a substantially similar functionality compared to other types of siRNA. Additionally, an shRNA is not considered a modified siRNA unless the nucleotides include modifications as described in more detail below. In cases in which the siRNA is presented as a hairpin shRNA, the size and orientation of the strands can vary. Additional information regarding shRNA can be found in the incorporated reference U.S.

patent application Ser. No. 11/283,484, entitled APPARATUS AND SYSTEM HAVING DRY GENE SILENCING COMPOSITIONS, with Barbara Robertson, Ph.D., et al. as inventors.

In one embodiment, the present invention includes siRNA having a modification that increases specificity for gene silencing. Accordingly, specificity modifications can be incorporated into any siRNA in order to decrease off-targeting. Such specificity modifications can be an aspect of on-targeting. A more complete description of specificity modifications can be found in the incorporated reference U.S. patent application Ser. No. 11/283,484, entitled APPARATUS AND SYSTEM HAVING DRY GENE SILENCING COMPOSITIONS, with Barbara Robertson, Ph.D., et al. as inventors.

An example of a specificity enhancing chemical modification can include 2' modifications at the first and second sense nucleotides and can include a phosphoryl moiety on the 5' carbon at the antisense 5' terminal nucleotide. A second example can include 2' modifications at the first and second sense nucleotides and at the first and second antisense nucleotides, and can include a phosphoryl moiety on the 5' carbon at the antisense 5' terminal nucleotide. A third example can include 2' modifications at the first and second sense nucleotides and at the second antisense nucleotide, and can include a phosphoryl moiety on the 5' carbon at the antisense 5' terminal nucleotide. A fourth example can include a 5' deoxy group modification on the sense 5' terminal nucleotide, and 2' modifications at the first and/or second antisense nucleotides with or without 2' modifications at the first and second sense nucleotides, as well as a phosphoryl moiety on the 5' carbon at the antisense 5' terminal nucleotide. Furthermore, including the modification of the phosphate group on the 5' carbon of the first antisense nucleotide in the absence of any 2' modifications can impart some benefit for reducing off-targeting. In some instances it can be preferable for the 5' carbon at the sense 5' terminal nucleotide to not have a phosphate group.

For example, on-target modifications can include 2'-O-methyl on nucleotide positions one and two (e.g., first position and second nucleotide at the 5' end) of the sense strand and a 5' phosphate on the antisense strand. Additionally, the on-target modifications can include a 2' modification on the nucleotide at position one and/or two of the antisense strand (i.e., the second nucleotide from the 5' end of the antisense strand), and a phosphate moiety at the 5' position of the 5' terminal nucleotide of the antisense strand. A preferred modification includes a 2' modification at the first and second sense nucleotides and at the second antisense nucleotide, and a phosphate on the antisense 5' terminal nucleotide.

In one embodiment, the present invention includes siRNA having stability enhancing modifications. As such, the stability modifications can be used with or without specificity modifications, and vice versa. Additionally, siRNA having stability modifications can be advantageous because they can prevent degradation by nucleases. Accordingly, the stability modifications can increase the potential shelf life of siRNA, and increase the ability to manufacture and store plates having dry gene silencing compositions for extended periods of time. A more complete description of stabilizing modifications can be found in the incorporated reference U.S. patent application Ser. No. 11/283,484, entitled APPARATUS AND SYSTEM HAVING DRY GENE SILENCING COMPOSITIONS, with Barbara Robertson, Ph.D., et al. as inventors.

In one embodiment of the present invention, the siRNA can include a conjugate, such as a label, coupled to the sense and/or antisense strands. The conjugate can perform a variety of functions or provide additional benefits to the siRNA. For example, a cholesterol conjugate can increase the penetration of the siRNA through a cell membrane with or without being complexed with a carrier. Additionally, the conjugates can be labels that can be monitored or identified in order to determine whether or not a labeled siRNA entered a cell. A complete description of conjugates that can be coupled to siRNA can be found in the incorporated reference U.S. patent application Ser. No. 11/283,484, entitled APPARATUS AND SYSTEM HAVING DRY GENE SILENCING COMPOSITIONS, with Barbara Robertson, Ph.D., et al. as inventors.

V. Polynucleotide Carriers

In one embodiment, the present invention includes polynucleotide carriers that can interact with siRNA, and transport the siRNA across a cell membrane. However, in other embodiments of the invention modes of transfection can be implemented without carriers, such as by electrophoresis, precipitation, particle bombardment, optoporation, and microinjection. Usually, polynucleotide carriers include a positive charge that interacts with the negatively charged phosphates on the polynucleotide backbone. Polynucleotide carriers that are well known in the art of cellular nucleic acid deliver. Preferred polynucleotide carriers include cationic polymers, lipids, lipopolymers, lipid-peptide mixtures, and the like that are capable of complexing with an siRNA and delivering the siRNA into a cell in a manner that retains the gene silencing functionality without being overly toxic.

In one embodiment, lipids or lipid-peptide mixtures are preferable for introducing an siRNA into a target cell. Typically, the lipid is a cationic lipid. Cationic lipids that can be used to introduce siRNA into cells can be characterized by having little or no toxicity (e.g., defined as less than 15-20% toxicity), which can be measured AlamarBlue or equivalent cell viability assays. Such lipids can facilitate delivery of sufficient amounts of siRNA into cells in order to induce gene silencing. Peptides that have affinity to one or more proteins, lipids, lipid-polysaccharide, or other components of the cell membrane can be conjugated to the siRNA and used independent of lipids or advantageously combined with one or more lipids to form a polynucleotide carrier. Such lipid-peptide mixtures can enhance RTF of siRNA. Cholesterol conjugates can be similarly coupled to the siRNA and be used independent of polynucleotide carriers or advantageously combined therewith.

For example, suitable lipids for siRNA pool RTF include OLIGOFECTAMINE™, TransIT-TKO™, or TBIO Lipid 6™, LIPOFECTAMINE™ 2000, lipids DharmaFECT™ 1, DharmaFECT™ 2, DharmaFECT™ 3, and DharmaFECT™ 4 (Dharmacon, Inc.). The term "DharmaFECT™" (followed by any of the numerals 1, 2, 3, or 4) or the phrase "DharmaFECT™ transfection reagent," refers to one or more lipid-based transfection reagents that have been optimized to transfect siRNA rather than larger nucleic acids (e.g., plasmids). Additional information on lipids can be obtained in U.S. Pat. Nos. 5,674,108, 5,834,439, 6,110,916, 6,399,663, and 6,716,582, and international publications WO 00/12454 and WO 97/42819, wherein each is incorporated herein by reference.

The formation of a functional siRNA-lipid complex can be prepared by combining siRNA and the lipid. As such, an appropriate volume of lipid at a selected concentration can be combined with a volume of media and/or buffer to form a lipid-media or lipid-buffer having a suitable concentration of lipid. For example, a volume of lipid media ranging from about 5-50 microliters ("uL") can include about 0.03-2 micrograms ("ug") of lipid to be introduced into each well of a 96-well plate, and the amount of lipid can be changed to correspond with other well sizes. The choice of media and/or buffer can improve the efficiency of the RTF protocol. Some media contain one or more additives that induce cell toxicity and/or non-specific gene modulation during RTF. Examples of preferred media or buffers include Opti-MEM™ (GIBCO, Cat. # 31985-070), HyQ-MEM-RS™ (HyClone, Cat.# SH30564.01), Hanks Balanced Salt Solution™, or equivalent media.

The lipid-media or lipid-buffer can be introduced into a well by a variety of methods including hand-held single and multi-channel pipettes, or more advanced and automated delivery systems that can inject measured volumes of the lipid solution into a well. The lipid solution can be incubated in the well that contains the dried gene silencing composition for a period of time that is sufficient to solubilize or suspend the siRNAs, and to form siRNA-lipid complexes (e.g., lipoplexes). In general, the process of siRNA solubilization and lipoplex formation can require about 20 minutes, but usually not more than 120 minutes. The complex formation process is generally performed at room temperature, but typically is performed at temperatures ranging from 4-37° C. In some instances, the lipid and siRNAs can be mixed by agitating the plate (e.g., swirl, vortex, sonicate) for brief periods (e.g., seconds to minutes) to enhance the rate of siRNA solubilization and complex formation.

VI. Biological Agents

In one embodiment, the present invention includes biological agents that can be studied for their effect on cells that have had a particular gene or combination of genes silenced with siRNA. Accordingly, a biological agent can be introduced to a cell or to the cell culture medium to determine whether or not the silencing of a particular gene alters the effect of the biological agent on the cell compared to a cell that does not have a gene silenced. Also, the effects of silencing multiple genes in a single cell or different genes in different cells can be compared so that a broad spectrum analysis of the biological agent can be obtained. Moreover, the entire genome of any organism can be screened for being associated with a response to a biological agent. The biological agents in accordance with the present invention can be substances that are physiologically active agents, such as molecules or combinations of molecules, or microorganisms that are benign or pathologic in nature.

A. Active Agents

In one embodiment, the biological agent is an active agent, which includes substances known or suspected of having biological or physiological activity. That is, the substance can interact with proteins, cells, lipids, polypeptides, and the like within an organism and cause a change in the organism. Active agents include a wide variety of molecules and combinations of molecules including small molecules that can be used as drugs, chemicals that can have adverse or beneficial physiological interactions, nucleic acids like plasmid DNA, and polypeptides or proteins like enzymes, cytokines, and hormones. Additionally, macromolecular substances or structures, such as polymers, can be used. For example, a cellular response to latex can be studied in the presence of gene silencing. Accordingly, any active agent can be used in the present invention in order to be studied in the presence of gene silencing. This allows the selective silencing of a specific gene to identify genes that may be responsible for proteins or pathways that respond to the presence of the active agent.

In one embodiment, the active agent is a drug, which includes known substances that are used as drugs as well as substances suspected of being usable as drugs. As such, the drug can be studied by being introduced to cells that have a selected gene or combination of genes silenced wherein the drug can interact with external or internal components of a cell. This can allow for the activity of the drug to be assessed in the absence of selected gene products. For example, a disease model can be created by the selective silencing of a single gene or family of genes, and the drug can be administered to the cell so that its ability to function as a therapeutic agent can be monitored. In another example, a gene product suspected of adversely interacting with a drug can be silenced to determine the effect of the drug on the cell in the absence of the gene product. Additionally, a single drug can be studied with different genes being silenced so that phenotypic changes can be related to drug activity. Thus, a wide array of studies can be performed on drug activity in the presence of a silenced gene.

In one embodiment, the active agent is a chemical other then a drug. The chemical can be known or suspected to have biological or physiological activity that is beneficial or adverse to an organism. As such, the chemical can be studied in the presence of a silenced gene or combination of genes so that the effect of the chemical on a cell can be determined. For example, a chemical suspected of having a toxic or detrimental effect on an organism can be tested on selected cell types from that organism, wherein various genes in the cells can be silenced so that the toxicity or cellular function can be monitored in the presence of the suspected toxin. This can be beneficial for identifying genes involved in a response to a toxic chemical. On the other hand, the same procedure could be used to identify biological pathways that adversely react to certain chemicals that may otherwise have a beneficial use.

In one embodiment, the active agent is a polypeptide or protein such as a hormone, enzyme, cytokine, or the like. As such, the active agent can be any naturally occurring or synthetic polypeptide that is known or suspected of having biological or physiological activity. Polypeptides can be studied in the present invention by being introduced to cells having a selected gene or combinations of genes that have been silenced. This can allow for a broad array of screenings of polypeptides and activities in various cellular conditions and cell phenotypes. For example, a polypeptide having a suspected therapeutic use can be studied with cells having selected genes silenced to determine which genes or family of genes may interact with the polypeptide. In another example, a disease model can be created by the selective silencing of a gene or genes in a particular pathway so that the activity or function of a polypeptide can be studied in the model. This can enable the activity of a polypeptide in response to a disease to be studied or identify polypeptides that can be used to treat the disease.

In one embodiment, the importance of one or more genes in the response of cells to a specific biological agent can be tested. Also, the importance of one or more genes in a particular phenotype (e.g., cell growth, cell recognition, cell differentiation) can be studied in the presence of a biological agent. For example, various genes in a cell can be silenced, such as genes of the human genome, a particular family of genes (e.g., kinase genes), or genes of a particular pathway. Subsequently, the ability of the cells to respond to a particular substance or compound (e.g., a drug or toxic chemical) that induces a measurable response can be tested and compared with untreated cells (i.e., cells not transfected with an siRNA) to assess the contribution of each gene to the response. In the instance cells fail to respond similarly to control cells, the method can identify a gene that plays a role in the cellular response to the substance or compound.

In one embodiment, a cellular response to an active agent can be compared between a test well having a test siRNA and a control well either devoid of any siRNA or having a control siRNA. A cellular response to the active agent can be measured or identified by comparing at least one of retention, excretion, metabolism, activity, or absorption of the active agent by the cells in the test well compared to the cells in the control well. Also, any change in cell function and/or morphology of the cells in the test well compared to the cells in the control well can be monitored and detected. Monitoring and/or detection can be done visually by the experimenter. Alternatively, monitoring and/or detection can be automated using technologies designed for HCS analysis.

In one embodiment, gene silencing can be used in a method for assessing the contribution of a gene to cellular interaction, retention, excretion, metabolism, or absorption with respect to the active agent. For example, cell cultures having a gene or combination of genes that have been silenced can be treated with a particular compound (e.g., a potential therapeutic compound or toxic compound). The ability of cells to retain, excrete, metabolize, absorb, or adsorb that compound can be measured and compared with cells that are not administered the compound or cells with no gene silencing. This can be used to identify one or more host genes that play a role in the pharmacokinetics of drugs used for the treatment of cancer, neurological diseases, diabetes, metabolic diseases, diseases of the bone, cartilage, muscle, heart, kidneys, liver, prostate, gastrointestinal tract, and more. Also, this can be used to identify genes that are involved in an immunological response to a toxic chemical, and/or genes that are involved in the pharmacogenetics of drug response.

Accordingly, the present invention can be used with a wide array of active agents and is not intended to be limited by the active agents described herein. As such, any chemical, drug, polypeptide, polynucleotide, and the like can be studied in the presence of selected cells by silencing a selected gene or combination of genes. Thus, any active agent can be a part of a system or kit that includes a well plate having a gene silencing composition that silences genes that may interact with the active agent.

In one embodiment, gene silencing in cells can be used to identify particular phenotypes that are generated by an active agent. Accordingly, the effect of the active agent on the cell can be determined when a specific gene or combination of genes has been silenced. This can be especially beneficial in the instance the silenced gene or combination of genes creates a disease model. As such, the effect of the drug on a cell can be monitored and identified instead of the effect of the cell on the drug (i.e., absorption, excretion, metabolism, and the like is not studied). Phenotypic changes in a cell that are generated by an active agent in the presence of gene silencing can be used to simulate the effect of a drugs in the absence of a gene product, and thereby can provide information related to whether or not certain active agents are suitable for a specific therapeutic regimen. Additionally, similar studies can be performed by administering multiple active agents in the presence of gene silencing.

B. Microorganisms

Microorganisms that interact with an organism or cell can be studied in accordance with the present invention by being introduced to cell cultures having a selected gene or combinations of genes that have been silenced. This can allow for a cellular response to such a microorganism to be studied when the production of a selected cellular polypeptide, such as a protein, has been silenced. Similarly, this protocol can enable one to identify the contribution of various host genes to a pathogenic infection. Also, this can allow for selected microorganism genes to be studied because the siRNA in the gene silencing composition can be used to silence a microorganism genomic gene. As such, a cell that has not had any host genomic genes silenced can be used to study microorganisms having silenced genes. This can allow for microorganism genomic genes that are vital to infection or pathogenic activity to be studied. Similarly, genes of a benign microorganism can be silenced. Thus, both benign and pathogenic microorganisms can be studied.

In one embodiment, the biological agent is a pathogen. The pathogen can be a microbe that can cause an infection associated with phenotypic changes, cellular toxicity, and death. Examples of pathogens include viruses, bacteria, yeasts, protozoa, and the like. Accordingly, a cellular response or contribution to an infection can be studied when a specific gene or combination of genes in the cell have been silenced. This can include silencing genomic genes of the cell or transgenes that have been stably or transiently transfected into the cell. Also, the gene being silenced can be genomic genes of the pathogen. This can allow for an infectious pathway to be studied when cellular or pathogenic genes have been silenced. Optionally, the pathogen can be used in an amount that is toxic to the cells, which can cause the cells to have inhibited cellular functions or cause cell death.

In one embodiment, the viability or function of a cell in a test well can be compared to a cell in a control well in response to gene silencing and the presence of a microorganism such as a pathogen. Also, the production or non-production of a target polypeptide in response to the pathogen can be detected in cells that have a target gene that is silenced and/or not silenced. Additionally, a determination can be made as to whether or not the target gene is involved in a pathogenic infection. Such a determination can be made when the test well contains living cells after incubation with the pathogen, which is an indication the target gene is involved in an infection by the pathogen. This can be especially useful when the pathogen is introduced to the cell in a toxic amount. Moreover, a test well that contains more living cells compared to the control well can be an indication the target gene is involved in at least one of pathogenic infection, pathogen replication, or pathogen release from the cells.

In one embodiment, the cellular mechanisms that contribute to a pathogenic infection can be detected by selectively silencing specific genes or combinations of genes. Accordingly, various aspects of a pathogenic infection can be identified by administering the pathogen to cells that have had a specific gene or combination of genes silenced. In the instance the pathogen is a virus it can be modified to contain a reporter vector which does not include viral genes that aid in the infection. This can allow for a selected host genomic gene or combinations of genes to be silenced so that the effect on viral infection can be determined because the virus will not have any infectious genes to use for inducing the infection. As such, the cellular mechanisms that contribute to the virus infecting the cell can be identified, which can allow for designing preventive therapies to inhibit the onset of such infections.

Additionally, gene silencing can be used to study various other aspects of interactions that occur between a cell and a microorganism. This can include the use of multiple types of microorganisms so that the cellular response to multiple modes of infection can be monitored and identified. Also, the studies can include monitoring and identifying genes involved in a cellular response to a pathogen when the cell has also received a drug, which can aid in understanding the process that a drug can inhibit an infection. Various other studies can be performed that use gene silencing to study cell and microorganism interactions.

VII. Sensitization Screens

In one embodiment, the present invention includes a method for determining a cellular response to a biological agent in the presence of gene silencing when the cell has been sensitized to the biological agent. Sensitization usually occurs after repeated exposure to a biological agent, which can be either an active agent or a microorganism. Sensitization can be detrimental when beneficial substances, such as drugs, begin to cause serious and unwanted physiological complications. Also, sensitization has been linked to chemical dependencies and addictions to various drugs. Moreover, sensitization by a microorganism can cause inflammation or other allergic reactions. Sensitization to a biological agent is typically manifested by an enhanced response following repeated administration of the same dose the biological agent. Accordingly, the same dose begins to cause increased cellular responses over time.

The mechanisms for such sensitizations can be identified and studied by silencing specific genes or combinations of genes in a cell. As such, the method of studying sensitization with gene silencing can be performed in substantially the same manner as the foregoing RTF protocols; however, the cells have been previously sensitized to the biological agent. The cells can be sensitized to the biological agent by repeated dosings that can be constant or varied from dose-to-dose. This can include sensitizing the cell to an active agent or a microorganism. Such sensitization studies are particularly well suited for HCS and HTS assays, and the information can be used in producing bioinformatics indicative of the genes associated with sensitization to the biological agent.

In one embodiment, a sensitization study can be performed in the presence of two biological agents. As such, the cell can be sensitized to one biological agent and the other biological agent can be a drug or potential drug to reduce the sanitization. Accordingly, a potential therapeutic agent can be screened with the sensitizing biological agent so that the sensitization can be studied. Thus, the genes involved in the sensitized cellular response can be studied in the presence of the potential therapeutic agent. Additionally, gene silencing can be used to identify the genes involved in the cellular response to the potential therapeutic agent in the presence of the sensitizing biological agent.

For example, a neurological cell can be sensitized to cocaine. Cocaine is a well characterized psychostimulant that is highly addictive, and functions by blocking the re-uptake of dopamine in neurons, which contributes to its rewarding properties. Neurological cells can be sensitized with cocaine and monitored for increasing levels of dopamine in the culture. Genes encoding for polypeptides, such as kinases, adapter proteins, transcription factors, and the like, can be silenced before cocaine is administered. After cocaine is administered, an altered response can be indicative of genes that are responsible for the sensitization.

In one embodiment, the present invention provides a method of screening a library of siRNAs with a biological agent sensitized background. Typically, sensitized background studies are performed with drugs; however, they can also be performed with other types of biological agents. Accordingly, sensitized background screens can allow for a drug or potential drug that is toxic at therapeutic levels to be studied at levels below its traditional toxicity level. For example, a drug may have a particular detrimental effect on a cancer cell at a specific concentration, but the drug induces systemic toxicity when dosed at that concentration. As such, the functional concentration of the drug is too high to use as an anti-cancer therapeutic because of systemic toxicity. A sensitized background study can be performed by reducing the concentration of the drug (i.e., so there is no toxicity), while screening a library, such as an siRNA library and/or a drug library, to look for secondary targets that generate a particular phenotype. This can include silencing a library of genes in different cell cultures with a corresponding library of siRNA and then introducing the drug into the different cell cultures at various sub-toxic concentrations. Such sensitized background studies can allow for a lower concentration of the drug to be tested in the presence of gene silencing to generate a particular phenotype such as toxicity, change in morphology, or change in cell function. Additionally, various lower concentrations that are not overly toxic can be screened together in different cell cultures with a particular library of siRNAs. The use of an siRNA library screen performed in a drug sensitized background can be beneficial for identifying combinations of drug targets that are particularly effective from a therapeutic perspective. Also, the sensitized background siRNA library screens can be used to identify genes that are in the same pathway, in redundant pathways, or in mutually dependent pathways.

VIII. Synthetic Lethal Combinations

In one embodiment, the present invention includes determining a synthetic lethal combination of a silenced gene and a biological agent. Synthetic lethal combinations typically refer to two different stimuli that are benign or non-functional alone, but are lethal when combined. As such, a biological agent may not induce cellular toxicity, but is toxic when a gene has been silenced. Accordingly, the siRNA may silence a gene that encodes for a gene product that is vital for cell viability in the presence of the biological agent. Synthetic, lethal combinations can include a silenced gene produce and a biological agent, which can be either an active agent or a microorganism The mechanisms for such synthetic lethal combinations can be identified and studied by silencing specific genes or combinations of genes in a cell in the presence of a biological agent. As such, the method of studying of identifying lethal combinations with gene silencing can be performed in substantially the same manner as the foregoing RTF protocols. The combination of an active agent and a silenced gene may result in a lethal combination, wherein suitable cell viability is obtained in the absence of the active agent or the gene silencing. Similarly, microorganisms, such as viruses, can be studied to detect silenced genes that form a synthetic lethal with the microorganism. This may be used to detect gene products that are vital to be produced in the presence of the microorganism. Studies to detect synthetic lethal combinations are particularly well suited for cell viability, HCS, and HTS assays, and the information can be used in producing bioinformatics indicative of the genes associated with specific biological agents to generate the synthetic lethal combination.

In one embodiment, synthetic lethal combinations can be studied by combinations that results in a particular phenotype. Typically, the particular phenotype that results is cell death; however, decreased viability or compromised morphologies may be representative phenotypes. Accordingly, screening for synthetic lethal combinations can include introducing a biological agent into different cells that have a different gene or combination of genes that have been silenced. The synthetic lethal combinations can be identified by determining the combinations that generate a particular phenotype. As such, the genes identified with these phenotypic screens may or may not be related to the compound itself or how a normal cell would respond to the compound (e.g., excretion, metabolism, adsorption, absorption, and the like).

For example, a cell can be treated with paclitaxel and then administered siRNA to silence a gene or combination of genes. This can be used to identify synthetic lethals that are synergistic with paclitaxel. The identification of synthetic lethals that are synergistic with paclitaxel can be used to tailor therapies that use paclitaxel or avoid generation of synthetic lethals in patients that are administered paclitaxel. Also, the information can be used to generally improve the use of paclitaxel.

Additionally, the present invention includes generating libraries of active agents or microorganisms that have synthetic lethals or potential synthetic lethals with silenced genes. These libraries can be generated by employing the screening studies described herein that include silencing a gene or combination of genes in a cell and then administering a first biological agent to the cells. Subsequently, the same gene or combination of genes can be silenced in the same cell type, which is then administered a second biological agent. This process can continue until an entire library of biological agents, or microorganisms have been screened against the same silenced gene or combination of genes. This can be used to identify biological agents that have synergistic activities when combined with a silenced gene. This information can be implemented into bioinformatic software so that patterns of synthetic lethal combinations can be identified and monitored. Also, this can be used to test combinations of biological agents, such as a multi-drug combination, a toxin and drug combination, a polypeptide and drug combination, a polypeptide and toxin combination, a drug and pathogen combination, a polypeptide and pathogen combination, a combination of pathogens, and the like.

In one embodiment, a synthetic lethal combination can be identified and studied with a biological agent that can inhibit a gene function in combination with siRNA induced gene silencing. Accordingly, such a lethal combination can be identified and studied by employing an RTF protocol as described herein. Additionally, the biological agent, which can be an active agent or a microorganism, can be administered to the cells before, during, or after the siRNA induces gene silencing. Various combinations of inhibited gene functions and silenced genes can be screened for synthetic lethal combinations. While the synthetic lethal combinations can be assessed by cell viability, HCS and HTS applications can also be used.

IX. Well Arrangements

In one embodiment, RTF plates that include multiple wells having different dry gene silencing compositions can have the wells organized into predefined arrangements for testing a biological agent in the presence of gene silencing. Such arrangements can correspond to the type of assay being employed with the RTF plate and the number of variables being studied. For example, when a family of genes is being studied in the presence of an active agent or pathogen, the siRNA that targets a single gene can be organized in one column or row while pools of siRNAs targeting the gene can be organized in a different column or row. This format can be continued until siRNA targeting all the genes in a family for silencing are present, which may include multiple plates. Thus, the wells of a single plate or multiple plates can be organized into a pre-selected arrangement so that particular siRNAs are in a pre-selected pattern to show the activity of the biological agent when different genes have been silenced. The pre-selected pattern can include control wells, such as those that include one or more negative and/or positive siRNA controls, and transfection controls. Also, the pre-selected pattern can include wells that are empty or substantially devoid of siRNA, which can be used as controls and for calibrations.

It can be beneficial to have gene silencing compositions comprised of siRNA that are pre-dried in corresponding wells of different well plates so that multiple RTF plates can be prepared simultaneously. This can allow for RTF plates to have gene silencing compositions at standardized positions and amounts of siRNAs, which is beneficial for using standardized well plates in multiple experiments that can be conducted over time without introducing variability between the plates. The use of standardized plate arrangements can provide a series of plates that can be used over time and provide data that can be analyzed together. Also, it provides for the ability to use different biological agents in different plates so that the cellular responses of different biological agents in the presence of the same silenced gene can be identified.

For example, a plate comprising a plurality of columns of wells can include a transfection control in the first column, positive controls for RNAi in the second column, negative controls for RNAi in a third column, a pool of siRNA directed against a single target in a fourth column, and individual members of the siRNA pool that comprise the fourth column are in subsequent columns, such as the fifth through twelfth columns. Alternatively, the fifth through twelfth columns can comprise different concentrations of each siRNA in a pool, with the amount of siRNA increasing from well to well or decreasing from well to well. When a biological agent is studied in the presence of gene silencing on a plate having pre-defined arrangements of siRNAs, the array configuration may be used to easily identify which genes are responsible for cellular interactions with the biological agent or identifying which siRNA targeting a selected gene are more effective in regulating the cellular response to the biological agent.

In one embodiment, the well plate can be arranged so that the concentration of siRNA is constant through multiple wells in a column or row. This can allow for the biological agent to be studied at various concentrations in the presence of constant gene silencing. This can be beneficial for monitoring cellular responses to various concentrations or amounts of the biological agent when a specific gene or combination of genes has been silenced. Also, other similar variations of plate arrangements can be employed to study biological agents.

Figure 1B:
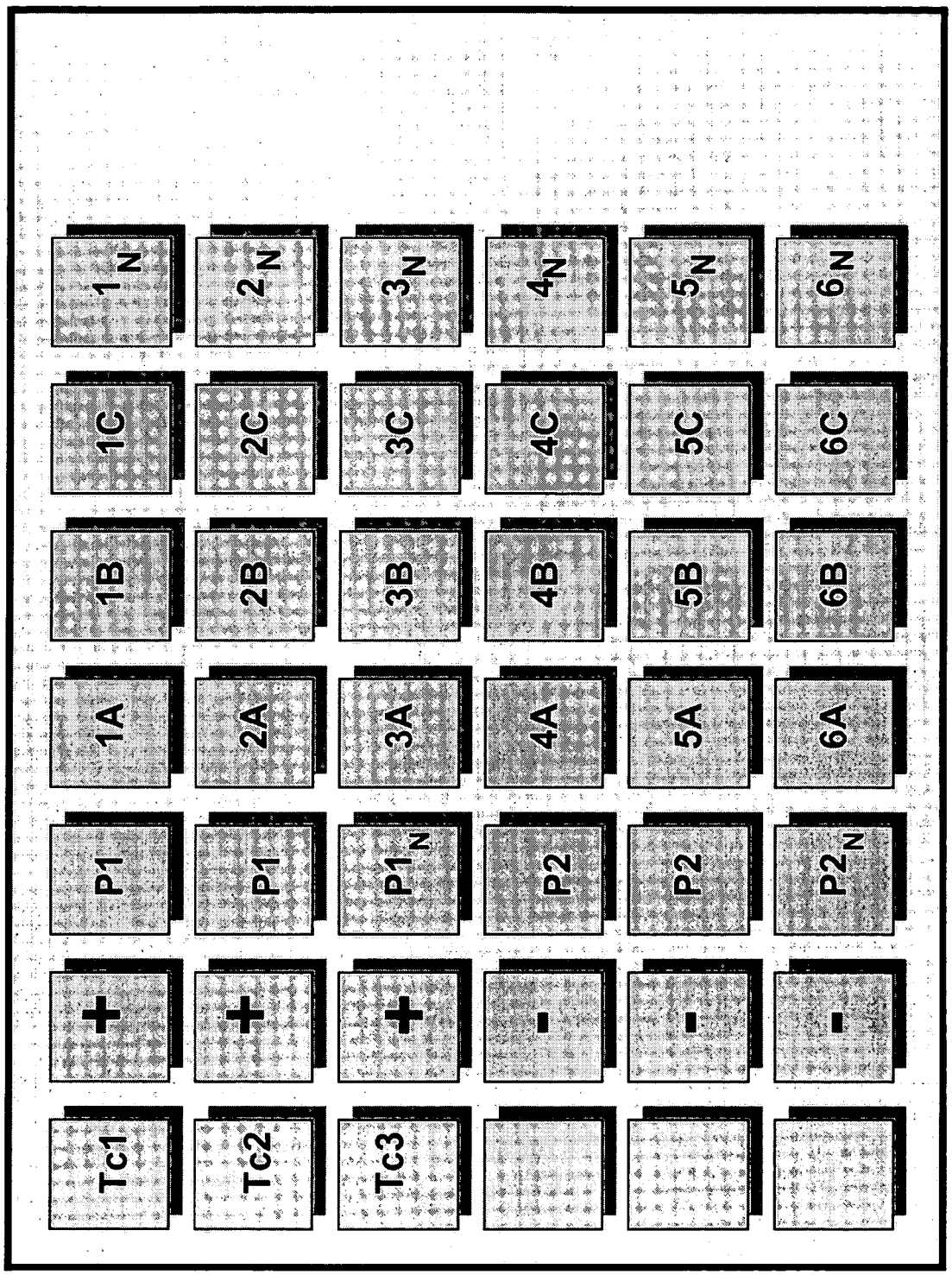

FIGS. 1A and 1B illustrate embodiments of plate arrangements similar with the foregoing concentrations arrangements for studying a biological agent. As shown, the plate arrangement can be useful for studying the effect of pools of siRNAs and individual siRNAs on a cellular response to a biological agent. While the wells are shown to be square, it should be recognized that they can be any shape. Also, the well plate can include any number of wells, and the number of wells depicted is merely for exemplification In the figures the wells are defined as follows: "Tc" indicates a transfection control well, wherein the increasing corresponding numbers identify different transfection controls; blank wells indicate wells devoid or substantially devoid of any siRNA; "+" indicates a positive control; "−" indicates negative controls; "P1" through "P1$_N$" indicate a first pool which silences a first gene at a concentration gradient; "P2" through "P2$_N$" indicate a second pool which silences a second gene at a concentration gradient; "1A" through "1$_N$" indicate a first individual siRNA of the first pool at a concentration gradient; "2A" through "2$_N$" indicate a second individual siRNA of the first pool at a concentration gradient; "3A" through "3$_N$" indicate a third individual siRNA of the first pool at a concentration gradient; "4A" through "4$_N$" indicate a first individual siRNA of the second pool at a concentration gradient; "5A" through "5$_N$" indicate a second individual siRNA of the second pool at a concentration gradient; and "6A" through "6$_N$" indicate a third individual siRNA of the second pool at a concentration gradient. Thus, FIG. 1A illustrates a well plate assaying a single pool, and FIG. 1B illustrates a well plate assaying multiple pools.

Figure 1C:
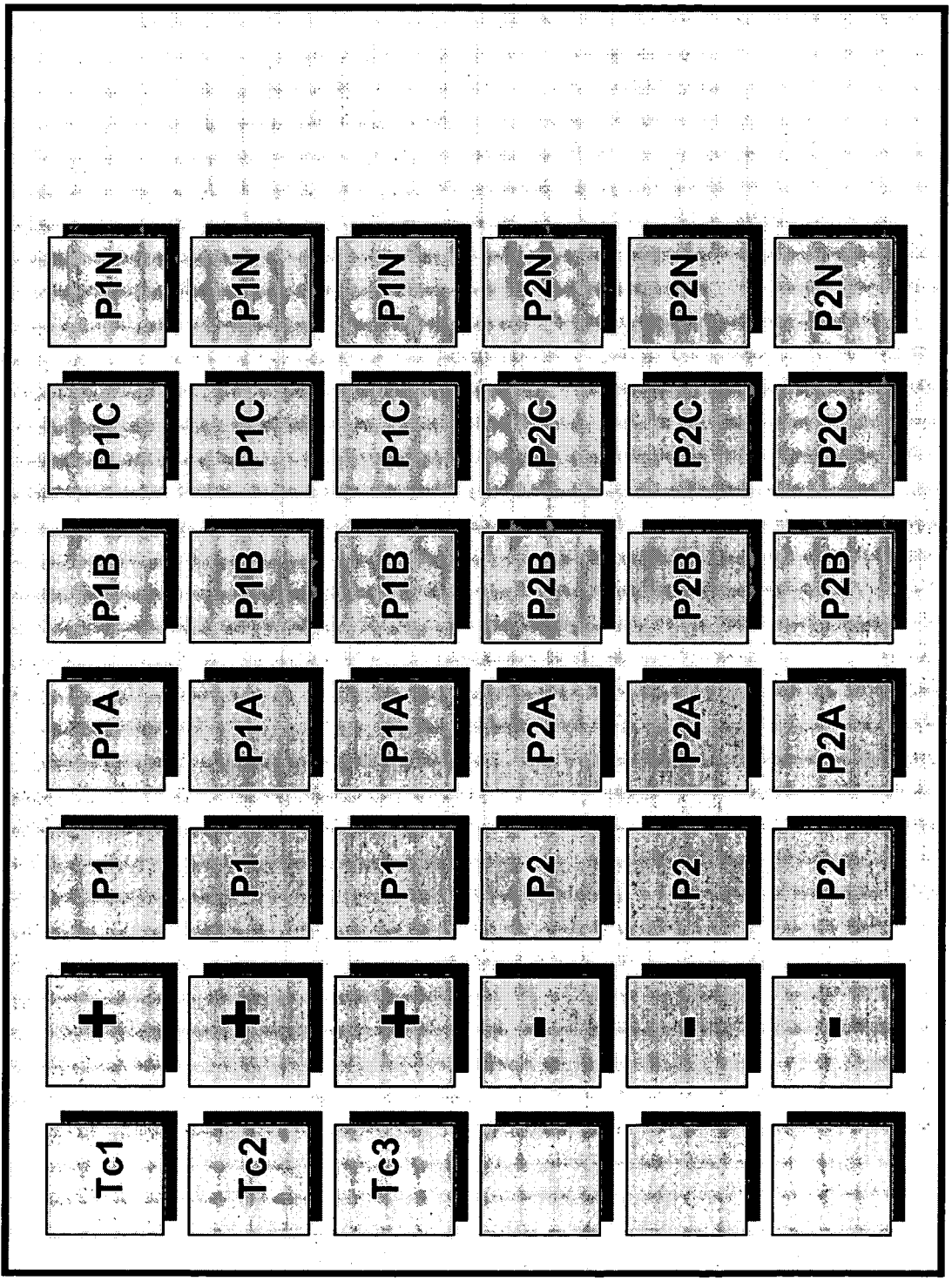

FIG. 1C illustrates another embodiment of a similar plate arrangement with the foregoing concentration arrangements for studying biological agents in the presence of gene silencing. The wells are defined as follows: "Tc" indicates a transfection control well, wherein the increasing corresponding numbers identify different transfection controls; blank wells indicate wells devoid or substantially devoid of any siRNA; "+" indicates a positive control; "−" indicates negative controls; "P1" indicates a first pool in triplicate which silences a first gene at a standard concentration; "P1A" through "P1N" indicates the first pool at a concentration gradient A-N, each in triplicate; "P2" indicates a second pool in triplicate which silences a second gene at a standard concentration; and "P2A" through "P2N" indicate the second pool at a concentration gradient A-N, each in triplicate. Accordingly, multiple wells can be used to test each gene silencing composition and/or condition for a response to the biological agent.

Figure 1D:
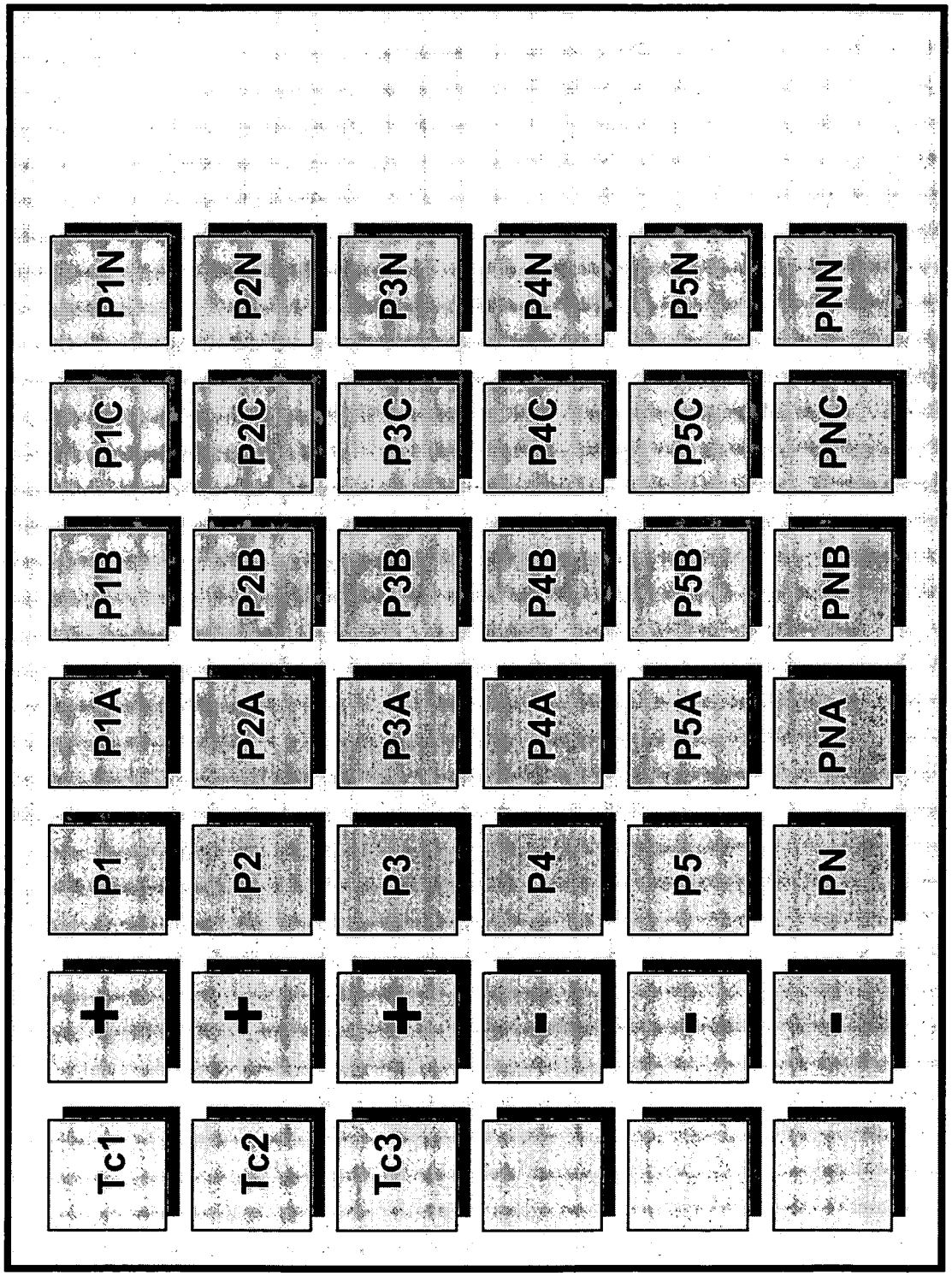

FIG. 1D illustrates an embodiment of a similar plate arrangement with the foregoing concentration arrangements for studying biological agents in the presence of gene silencing. The wells are defined as follows: "Tc" indicates a transfection control well, wherein the increasing corresponding numbers identify different transfection controls; blank wells indicate wells devoid or substantially devoid of any siRNA; "+" indicates a positive control; "−" indicates negative controls; "P1" through "PN" indicate a first pool which silences a first gene through an $N^{th}$ pool which silence an Nth gene at a standard concentration; and "P1A" through "P1N" indicate the first pool at a concentration gradient A-N, wherein second pool (e.g., "P2A" - "P2N") through $N^{th}$ pool (e.g., "PNA" -"PNN") each have a similar concentration gradient. Thus, the activity of a biological agent in response to gene silencing induced by multiple pools can be studied at different concentrations, wherein the multiple pools can be related or different.

Figure 1E:
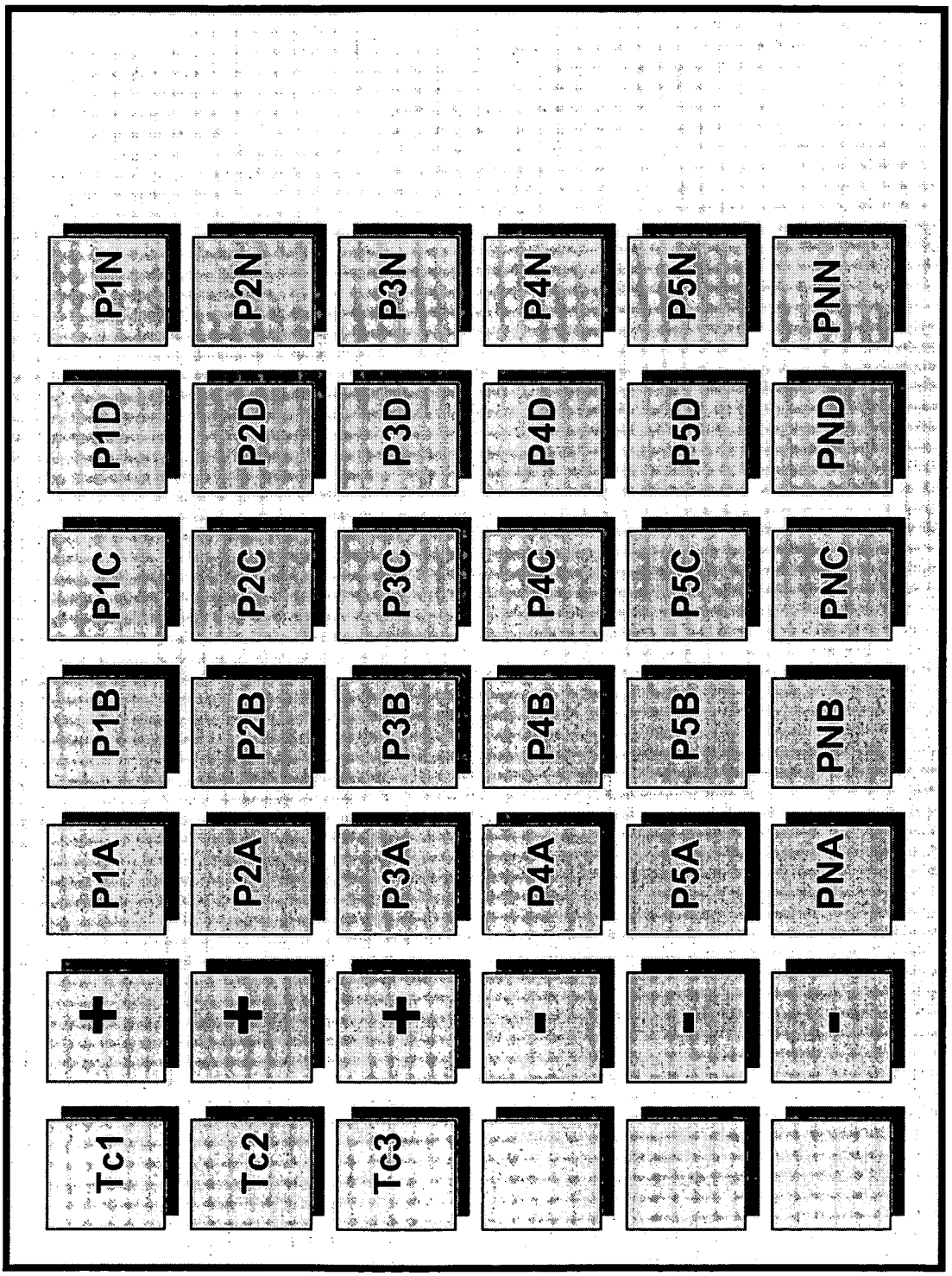

FIG. 1E illustrates an embodiment of a similar plate arrangement with the foregoing concentration arrangements for studying biological agents in the presence of gene silencing. The wells are defined as follows: "Tc" indicates a transfection control well, wherein the increasing corresponding numbers identify different transfection controls; blank wells indicate wells devoid or substantially devoid of any siRNA; "+" indicates a positive control; "−" indicates negative controls; "P1A" is a first pool that silences a first gene; "P1 B" is a second pool that silences the first gene; "P1C" is a third pool that silences the first gene; "P1D" is a fourth pool that silences the first gene; "P1N" is an $N^{th}$ pool that silences the first gene; "P2A" through "PNA" indicate a second through $N^{th}$ pools that silence related second through $N^{th}$ genes; and the corresponding wells in each of the "P2A" through "PNA" rows are A-N pools which silences the gene of the row. Thus, plates can be arranged with multiple pools targeting multiple related genes for silencing in order to study the activity of the biological agent under different gene silencing conditions.

Figure 2A:
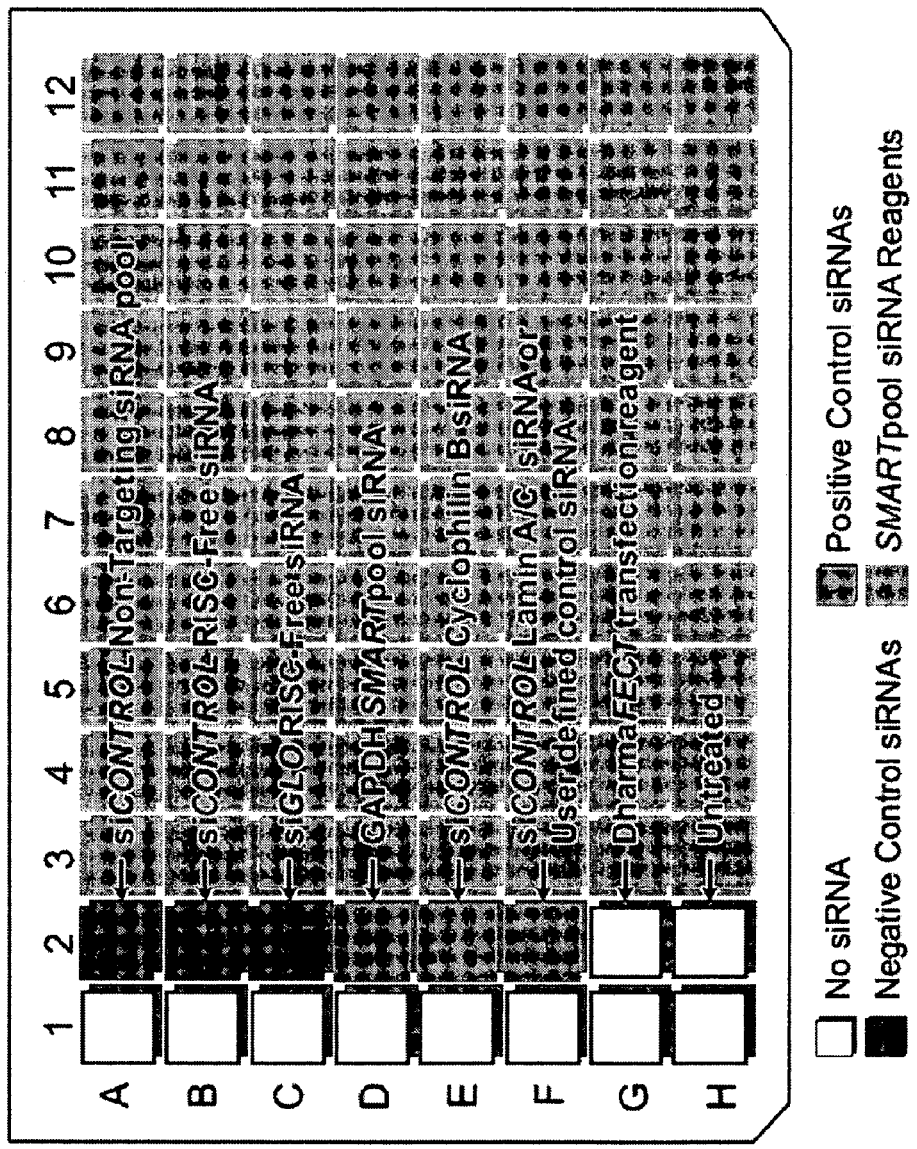
FIGS. 2A-2D are schematic diagrams that illustrate different embodiments of control plate arrangements that can be used to optimize studies of biological agents in the presence of gene silencing.

FIG. 2A is a schematic diagram that illustrates an embodiment of a well plate having control siRNA. Control siRNA can be useful in optimizing RTF protocols to be used with biological agents. As shown, wells A1-H1, G2, and H2 are blank wells devoid of siRNA. For example, wells A1-H1 are available for RTF testing controls. Well G2 can be used as a mock transfection control, and well H2 can be an untreated cell control. Wells A2-F2 contain negative and positive transfection control siRNAs. More particularly, the control wells include the following: well A2 includes a non-targeting negative control siRNA (e.g., siCONTROL™ Non-Targeting siRNA pool from Dharmacon, Inc.); well B2 includes an siRNA that inhibits being taken in and processed by RISC (e.g., siCONTROL™ RISC-Free from Dharmacon, Inc.); well C2 includes a dual control siRNA that can be used as a negative control and a transfection control (e.g., siGLO™ RISC-Free from Dharmacon, Inc.); well D2 includes a positive control siRNA targeting GAPDH control gene (e.g., siCONTROL™ GAPD from Dharmacon, Inc.); well E2 includes a positive control siRNA targeting cyclophilin B control gene (e.g., siCONTROL™ Cyclophilin B siRNA from Dharmacon, Inc.); and well F2 is a positive control siRNA targeting Lamin A/C control gene (e.g., siCONTROL™ Lamin A/C from Dharmacon). The wells in columns 3-12 can each contain a test siRNA or test siRNA pool such as any of Dharmacon's SMARTpool™ siRNA reagents. Alternatively, well F2 can be a user-defined control siRNA. This plate configuration can be useful for optimizing conditions for studying the effects of gene silencing with a single concentration of a biological agent.

Figure 2B:
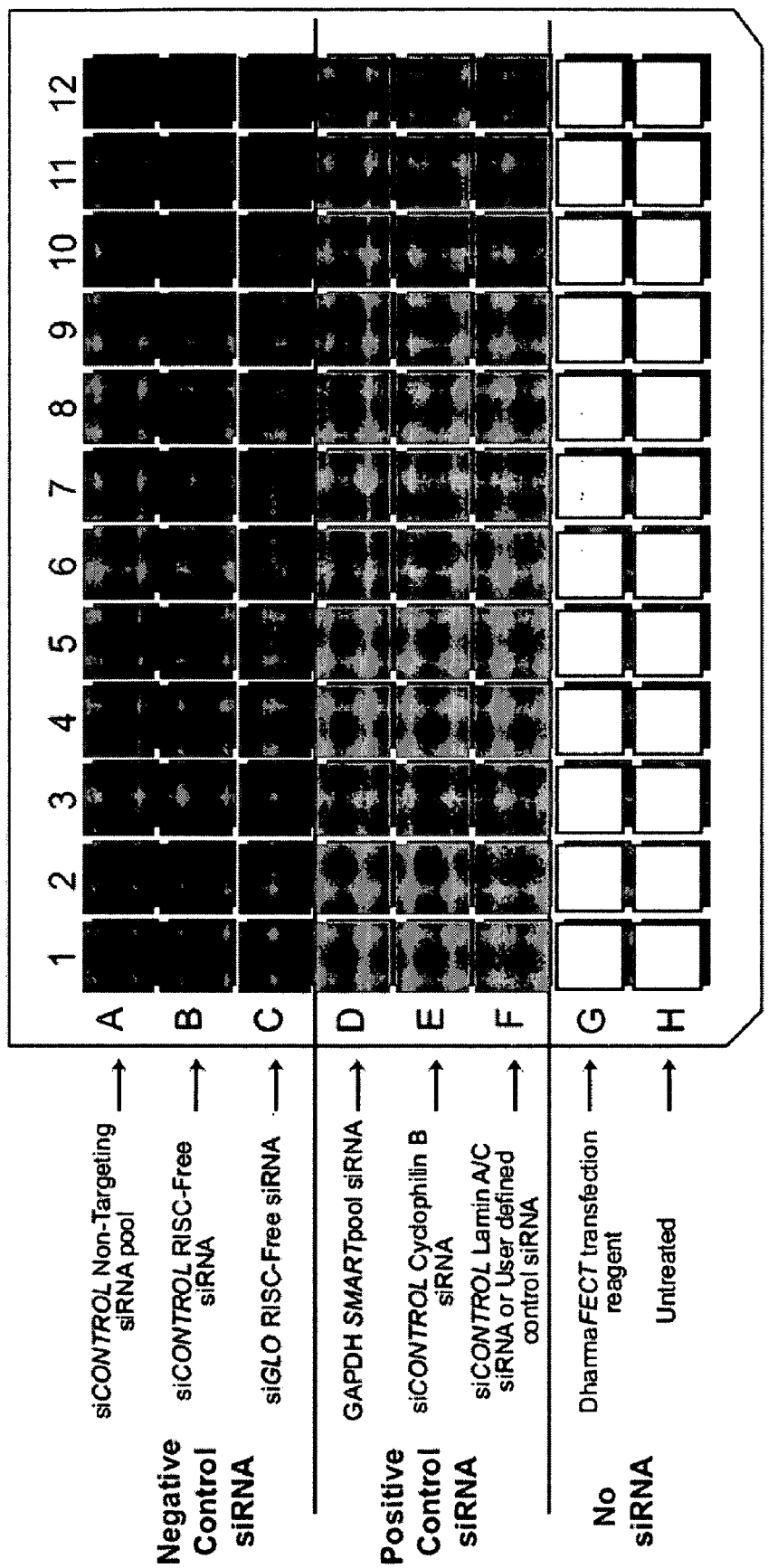

FIG. 2B is a schematic diagram that illustrates an embodiment of an optimization well plate or an RTF testing plate having control siRNA. The use of control siRNA can be beneficial for testing the efficacy of gene silencing experiments conducted to study the interaction of biological agents and cells. As shown, rows A-C can contain three negative control siRNAs (e.g., siCONTROL™ Non-Targeting siRNA pool, siCONTROL™ RISC-Free siRNA, siGLO™ RISC-Free siRNA, each from Dharmacon, Inc.). Rows D-E can contain three positive transfection control siRNAs (e.g., siCONTROL™ GAPD, siCONTROL™ Cyclophilin B siRNA, siCONTROL™ Lamin A/C siRNA, each from Dharmacon, Inc.). Alternatively, Row F can be a user defined control siRNA. Row G does not contain siRNA and can be used for mock-transfected cells in order to study the effect of the transfection reagent alone on cell viability and/or mRNA expression. Row H does not contain siRNA and is can be used for untreated cells, and can serve as a 100% viability control and/or 100% mRNA level control. Thus, the illustrated control plate arrangement can be beneficial to optimize conditions for studying the biological agent.

Figure 2C:
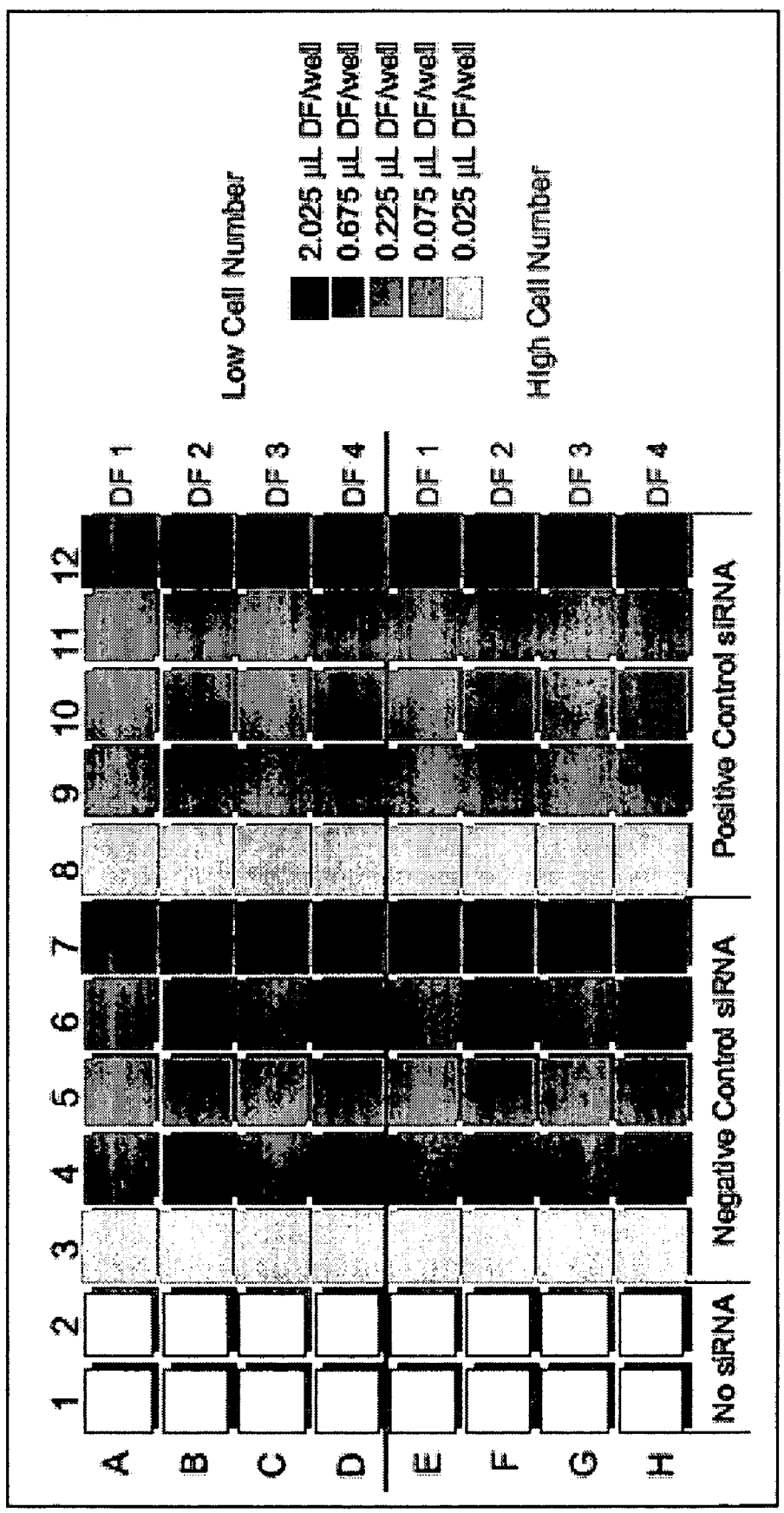

FIG. 2C is a schematic diagram that illustrates an embodiment of an optimization plate or an RTF testing plate having control siRNA that can be used to study a biological agent. The testing plate includes an arrangement of wells that can be used in a procedure for optimizing RTF conditions. As shown, column 1 is devoid of siRNA, and can be used as a blank that does not receive cells. This column can be used for a standard curve or other experimental controls that may be desired for an RTF testing protocol for assessing the efficacy of gene silencing. Column 2 is devoid of siRNA, but receives cells. This column can be used as an untreated reference for different volumes of polynucleotide carrier, such as Dharma-FECT™ transfection reagent, which is tested in columns 3-12. Columns 3-7 can contain negative control siRNAs, which serve as negative control samples for each Dharma-FECT™ transfection reagent volume used. As shown, up to five volumes of each DharmaFECT™ transfection reagent may be tested in one plate. In each row, the DharmaFECT™ transfection reagent volumes in columns 3-7 can be repeated in columns 8-12. This can allow the negative control siRNAs to serve as references for any gene silencing that occurs in the wells of columns 8-12, which contain positive transfection control siRNAs. Additionally, rows A-D can be seeded with a low cell density, and rows E-H can be seeded with a high cell density. Thus, the plate can include a combination of different RTF conditions, which can be used to determine the optimal amount of DharmaFECT™ transfection reagent, DharmaFECT™ transfection reagent volume, and cell number. Thus, various controls can be used to test the efficacy of an experiment that studies a biological agent in the presence of gene silencing.

Figure 2D:
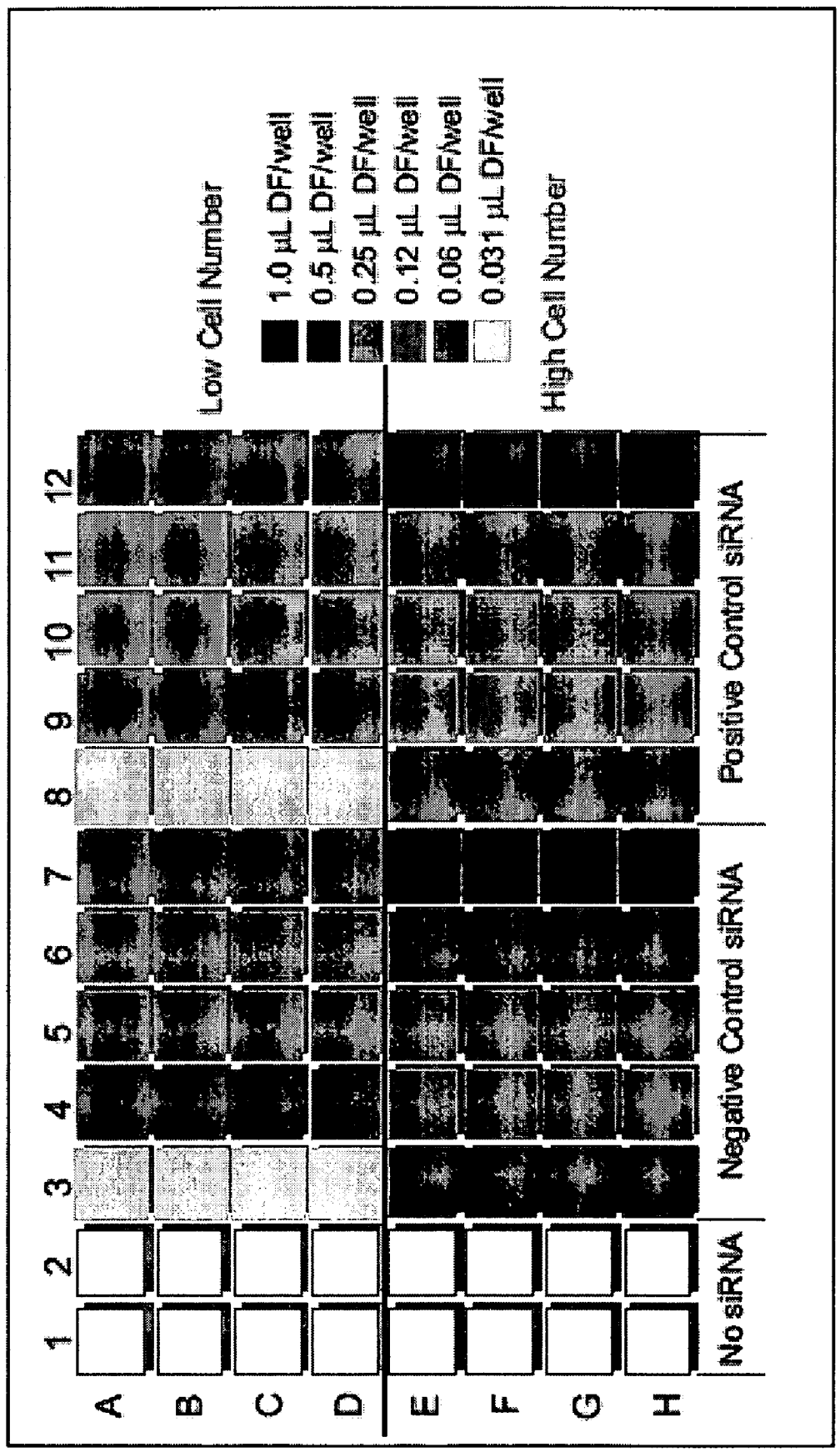

FIG. 2D is a schematic diagram that illustrates an embodiment of an optimization well plate or an RTF testing plate having control siRNA that can be used to study a biological agent. As shown, the plate is arranged with blanks, negative control siRNA, and positive control siRNA as in FIG. 2C. However, this plate can be assayed with different polynucleotide carrier concentrations. Rows A-D can be used with low cell densities with DharmaFECT™ transfection reagent at volumes ranging from 0.03 uL/well (e.g., columns 3 and 8) to 0.5 uL/well (e.g., columns 7 and 12). Rows E-H can be used with high cell densities with DharmaFECT™ transfection reagent at volumes ranging from 0.06 uL/well (e.g., columns 3 and 8) to 1.0 uL/well (e.g., columns 7 and 12). Thus, various parameters, such as lipid concentration and cell density, can be used to optimize conditions for studying a biological agent in the presence of gene silencing.

In the instance a well plate has a pre-defined arrangement of test and control siRNAs, it enables the contribution of each gene, member of a family of genes, each gene in a pathway, and/or each gene in a genome to be studied with respect to activity or response to a biological agent. Gene silencing experiments can be designed for identifying one or more host (e.g., human) genes that contribute to the ability of a virus, such as the HIV virus, to infect human cells. Alternatively, the siRNA in the gene silencing composition can be directed to the viral genes so that the viral infectious pathway can be studied. As such, studies can be performed in cells that are susceptible to HIV infection (e.g., JC53 cells), wherein the HIV virus is added to the cells before, during, or after gene silencing. For example, after culturing the cells for a period of 24-48 hours, the cells in each well can be subjected to a lethal titer of the HIV virus. Following an appropriate incubation period for infection, the cellular response to the HIV can be studied by detecting the presence and/or amounts of targeted polypeptides. Test wells that contain living cells or a substantially larger number of living cells than control wells can be used to identify a host gene that is necessary for viral infection, replication, and/or release. A similar study can be performed to study the viral genes involved in the pathogenic infection. These types of studies can be extended to any microorganism.

In one embodiment, a plate can have an arrangement of gene silencing compositions containing siRNA directed against a gene or genes whose silencing is known to induce a particular disease state. Also, multiple disease models can be created on a single plate by inducing selected gene silencing. This can allow for biological agents to be studied in single or multiple disease models on a single plate. Examples of diseases models that may be included by gene silencing include those associated with cancer, neurological diseases, diabetes, metabolic diseases, diseases of the bone, cartilage, muscle, heart, kidneys, liver, prostate, gastrointestinal tract, and the like.

As described, the well plate arrangements can be organized in order to study the effects of gene silencing induced by libraries of siRNAs in the presence of biological agents. Examples of such siRNA libraries can be reviewed in Table 1.

TABLE 1

SIRNA LIBRARIES

| Plate(s)/Pathway | Number of Genes |
|---|---|
| Human Genome | ~22,000 |
| Human Druggable Set | 7309 |
| Protein Kinases | 779 |
| Tyrosine Kinases | 85 |
| Calcium/Calmodulin Protein Kinase (CaMK) | 71 |
| CMGC Kinases | 60 |
| AGC Kinases | 59 |
| Mitogen-Activated Protein Kinase (MAPK) | 58 |
| S-T Kinases | 54 |
| Proteases | 514 |
| Serine Proteases | 128 |
| Metallo Proteases | 128 |
| Cysteine Proteases | 74 |
| G-Protein Coupled Receptors | 518 |
| Apoptosis | 318 |
| Ion Channels | 286 |
| Phosphatases | 193 |
| Cytokine Receptors | 166 |
| Membrane Trafficking/Remodeling | 122 |
| Cell Cycle Regulation | 111 |
| Deubiquinating Enzyme | 106 |
| Undifferentiated Cancer | 69 |
| Neoplastic Tissue | 67 |
| Nuclear Receptor | 49 |
| Insulin Signaling Pathway | 31 |
| Protein Hydroxylase | 24 |

Descriptions of siRNAs comprising the siRNA libraries in Table 1, and more complete descriptions of the use of gene silencing to study the plates/pathways identified in Table 1 are provided in U.S. Provisional Application Ser. No. 60/678,165. Moreover additional descriptions of plate arrangements and the types of genes that can be studied using siRNA are provided in U.S. Provisional Application Ser. No. 60/678,165, U.S. patent application Ser. No. 11/283,484, entitled APPARATUS AND SYSTEM HAVING DRY GENE SILENCING COMPOSITIONS, with Barbara Robertson, Ph.D., et al. as inventors, and U.S. patent application Ser. No. 11/283,482, entitled APPARATUS AND SYSTEM HAVING DRY GENE SILENCING POOLS, with Barbara Robertson, Ph.D., et al. as inventors. Any gene can be silenced in order to study the effect of a biological agent in the absence of the particular gene product.

EXAMPLES

The following examples are provided to describe some embodiments of the present invention in a manner that can be use by one of skill in the art to practice the present invention. Additional examples and supplementary information for the following examples can be reviewed in the incorporated references U.S. patent application Ser. No. 11/283,484, entitled APPARATUS AND SYSTEM HAVING DRY GENE SILENCING COMPOSITIONS, with Barbara Robertson, Ph.D., et al. as inventors, U.S. patent application Ser. No. 11/283,482, entitled APPARATUS AND SYSTEM HAVING DRY GENE SILENCING POOLS, with Barbara Robertson, Ph.D., et al. as inventors, U.S. patent application Ser. No. 11/283,483, entitled APPARATUS AND SYSTEM HAVING DRY CONTROL GENE SILENCING COMPOSITIONS, with Barbara Robertson, Ph.D., et al. as inventors, and U.S. Provisional Application Ser. No. 60/678,165.

Example 1

The genes involved in the kinase pathway are studied by siRNA RTF to determine the genes responsible for cell viability in the presence of a drug. Rationally designed pools of siRNAs targeting the 779 members of the kinase family are solubilized in RNase-free water and dried in individual wells of PLL coated 96-well plates. The amount of each pool of siRNA is a total of approximately 25 nM for 125 uL of total solution. A lipid solution having 0.1 ug of DharmaFECT™ 1 lipid in 25 uL total volume of Hanks Balanced Saline Buffer is added to each well and incubated for 20-40 minutes to solubilize and complex the siRNA before 10,000 HeLa cells in media are added for a final volume of 125 uL. The drug is added to the plates between 0 and 24 hours after the cells are added. The plates are then maintained between 24 and 72 hours and assayed for cell viability. A comparison between the cell viability of different cell cultures that were treated with the drug can be made to identify siRNA that silence genes that are essential for HeLa cell viability in the presence of the drug.

Example 2

The genes involved in the cytokine receptor family are studied by siRNA RTF to determine the genes responsible for cell viability in the presence of a drug. Rationally designed pools of siRNAs targeting the 166 members of the cytokine receptor family are solubilized in RNase-free water and dried in individual wells of PLL coated 96-well plates. The amount of each pool of siRNA is a total of approximately 25 nM for 125 uL of total solution. A lipid solution having 0.1 ug of DharmaFECT™ 1 lipid in 25 uL total volume of Hanks Balanced Saline Buffer is added to each well and incubated for 20-40 minutes to solubilize and complex the siRNA before 10,000 HT-29 cells in media are added for a final volume of 125 uL. The drug is added between 0 to 24 hours after the cells are added to the wells. The plates are maintained between 24 and 72 hours and assayed for cell viability. A comparison between the cell viability of different cultures that were treated with the drug in the presence of gene silencing induced by using different members of the cytokine receptor siRNA array can provide the identification of genes that are essential for HT-29 cell viability in the presence of the drug.

Example 3

The effect of human growth hormone on cell differentiation can be studied by silencing genes in the phosphatase family. As such, rationally designed siRNAs targeting the 193 members of the phosphatase family are solubilized in RNase-free water and dried in individual wells of PLL coated 96-well plates. The amount of each siRNA is measured to obtain a final siRNA concentration of approximately 25 nM. About 0.1 ug of DharmaFECT™ 1 lipid in 25 uL total volume of Hanks Balanced Saline Buffer is added to each well and incubated for 20-40 minutes to solubilize the siRNA(s) and create complexes before about 10,000 3T3 cells are added to obtain a final volume of 125 uL. The cells are then cultured for a period between 24 and 72 hours before human growth hormone (hGH) is added to selected cells. After 5-7 days, the cells are then lysed with a buffer containing 0.5% (v/v) Triton X-100, and adipose conversion is quantified by assaying the adipogenic enzyme, glycerophosphate dehydrogenase. Cells dosed with hGH that contain enzymatic activities below cells not receiving any hGH can be used to identify genes encoding for phosphatases that are essential 3T3 differentiation into adipocytes.

Example 4

Selected gene products that may be involved in a cellular response to an HIV virus can be studied by inducing silencing of the genes in the presence of the virus. This can be accomplished with rationally designed siRNAs that target the selected genes of the human genome. The selected genes are solubilized in RNase-free water and dried in individual wells of PLL coated 96-well plates. The amount of each siRNA added to each well is measured to obtain a final concentration of approximately 25 nM. About 0.1 ug of DharmaFECT™ 1 lipid in 25 uL total volume of Hanks Balanced Saline Buffer is added to each well and incubated for 20-40 minutes to solubilize the siRNA(s) and create complexes before about 10,000 JC-53 cells are added to each well to obtain a final volume of 125 uL. The cells are cultured for about 24 hours before an HIV virus at a toxic titer are added (e.g., moiety of infection ("MOI") sufficient to induce 99% cell death). The cells are then incubated for an appropriate period of time to induce cell death in control cultures (e.g., no siRNA or having control siRNA). Following the incubation, cell viability is measured in each well using AlamarBlue. Cells exhibiting lower amounts of cell death than control wells identify host genes that encode for proteins that may be necessary for HIV virus proliferation.

Example 5

A single plate or multiple plates containing an arrangement of gene silencing compositions can be used to determine whether gene silencing affects cell differentiation. For example, gene silencing compositions having siRNA that function as miRNA inhibitors can be used to study cell differentiation. After the siRNA have been solubilized or suspended in an aqueous medium, about 10,000-25,000 3T3-L1 mouse pre-adipocyte cells can be added to each well. After sufficient gene silencing, the cells can be treated with a cocktail of dexamethasome, insulin, and IBMX. About four days later, the cocktail can be replaced with media inoculated with insulin. About five days later, the cells can be stained with Sudan III-Oil Red, and the wells having different gene silencing compositions are scanned to identify cultures in which the cells have not differentiated into adipocytes. This can be useful in studying the effect of the miRNA pathway in cell differentiation.

Example 6

In one example, a multi-well RTF plate or series of plates can be designed in order to study a biological agent in the presence of gene silencing. Accordingly, the plates can be configured to include any of the following variables: (1) the concentration of individual or pools of siRNA can be between 0.01-250 nM, more preferably between 0.05 and 100 nM, even more preferably between 0.1 and 50 nM, still even more preferably between 0.5 and 25 nM, and most preferably between 0.75 and 10 nM or about 1 nM; (3) the types of polynucleotide carrier can be a lipid such as DharmaFECT™ 1, DharmaFECT™ 2, DharmaFECT™ 3, or DharmaFECT™ 4; (3) the concentration of the lipid polynucleotide carrier can be at concentrations of 0.05-1 ug per 100 uL of solution, more preferably at concentrations of 0.05-0.5 ug of lipid per 100 uL of solution, even more preferably still at concentrations of 0.05-0.25 ug of lipid per 100 uL of solution, and most preferably at concentrations of 0.05- 0.1 ug per 100 uL of solution; (4) the types of media and/or buffer used to complex the lipid can be preferably Opti-MEM™, more preferably HyQ-MEM™, and most preferably buffered salt solutions such as Hanks Buffered salt solution or equivalent mixtures; and (5) the types and amounts of cells having densities of 1,000 to 35,000 cells per about 0.3 0 $cm^2$ to about 0.35 $cm^2$ preferred densities of 2,000-30,000 cells per about 0.3 cm$^2$ to about 0.35 cm$^2$, more preferably 2,000-20,000 cells per about 0.30 cm$^2$ to about 35 cm$^2$, even more preferably 2,000-15,000 cells per about 0.30 cm$^2$ to about 0.35 cm$^2$, and most preferably cell densities of 2,000-10,000 cells per about 0.30 cm$^2$ to about 0.35 cm$^2$. Various amounts of biological agents can be tested on plates having any of the foregoing variables and variations in amounts of gene silencing.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of determining a cellular response to a biological agent, the method comprising:
    providing a well plate in a sealed, sterile package, the well plate being storable at a temperature of up to at least about 37° C. while maintaining functionality of a dried siRNA deposited therein, the well plate having a plurality of wells, including:
        a first control well with a dried control composition, wherein the dried control composition includes at least one of no siRNA, a positive control siRNA that is capable of targeting a known gene, a non-targeting negative control siRNA, an siRNA having at least one toxic motif, a non-functional siRNA, an siRNA that inhibits being taken in and processed by RISC, or a control siRNA that includes a fluorescent marker, the dried control composition being capable of being solublized or resuspended in an aqueous medium; and
        a first test well with a dried test gene silencing composition deposited therein that includes a test siRNA that is capable of silencing a first target gene, the dried test gene silencing composition being capable of being solublized or resuspended in the aqueous medium, the test siRNA comprising:
            a sense strand having 2'-O-methyl modifications on the first and second 5' nucleotides; and
            an antisense strand having a 2'-O-methyl modification on the second 5' nucleotide and a 5' end phosphate;
            wherein the sense region and the antisense region are capable of forming a duplex of 18-26 base pairs of nucleotides that has at least 80% complementarity over the range of the duplex, and wherein nucleotides of the sense strand and antisense strand other than the first 5' sense nucleotide, the second 5' sense nucleotide, and the second 5' antisense nucleotide include a 2'-OH;
    unsealing the package to expose the plurality of wells;
    adding the aqueous medium to the first control well and the first test well;
    solublizing or resuspending the dried test gene silencing composition and the dried control composition in the aqueous medium;
    adding cells to the first test well under conditions that permit transfection;
    adding cells to a first control well under conditions that permit transfection;
    adding a biological agent to the first test well and first control well, the biological agent being at least one of a known drug, a pro-drug, a candidate drug, a nucleic acid, a plasmid DNA, a polypeptide, a protein, an enzyme, a cytokine, a hormone, a polymer, a known cellular toxin, a suspected toxin, a microorganism, a virus, a bacterium, a yeast, a protozoan, or a sensitizing agent; and
    determining whether a first response to the biological agent by the cells in the first test well is different from a first control response to the biological agent by the cells in the first control well, wherein a condition of the first response being different from the first control response is an indication that the first target gene is involved in the response by the cell to the biological agent.

2. A method as in claim 1, further comprising culturing the cells in the first test well and first control well before adding the biological agent.

3. A method as in claim 2, wherein the culturing is from about 24 hours to about 48 hours.

4. A method as in claim 1, wherein the first test well and first control well each have a substantially flat well floor.

5. A method as in claim 1, wherein the cells express the first target gene.

6. A method as in claim 1, wherein the dried test gene silencing composition includes a pool of four siRNAs.

7. A method as in claim 1, wherein the test siRNA in the dried test gene silencing composition includes at least one of a conjugate or a hairpin structure.

8. A method as in claim 1, further comprising:
    sensitizing cells to the biological agent; and
    determining the effect of the biological agent on the sensitized cells.

9. A method as in claim 1, further comprising:
    screening a biological agent for a synthetic lethal combination; and
    identifying a synthetic lethal combination associated with the biological agent.

10. A method as in claim 1, wherein the biological agent is a microorganism.

11. A method as in claim 10, wherein the microorganism is a pathogen.

12. A method as in claim 11, wherein the pathogen is a virus.

13. A method as in claim 11, wherein the pathogen is added to the first test well and first control well in a lethal amount.

14. A method as in claim 11, wherein the first test well containing more living cells compared to the first control well is an indication that the first target gene is involved in at least one of pathogenic infection, pathogen replication, or pathogen release from the cells.

15. A method as in claim 12, wherein the virus includes a reporter vector.

16. A method as in claim 1, wherein a total amount of siRNA in the test siRNA in the dried test gene silencing composition is present in an amount for transfecting cells in only the first test well.

17. A method of determining a cellular response to an siRNA, the method comprising:
    adding an aqueous medium to a first test well in a well plate having a substantially dry gene silencing composition, the gene silencing composition having a test siRNA that is capable of silencing a first target gene, the dried test gene silencing composition being capable of being solublized or suspended in the aqueous medium in an amount sufficient for transfecting cells in the first test well, the test siRNA comprising:
        a sense strand having 2'-O-methyl modifications on the first and second 5' nucleotides; and
        an antisense strand having a 2'-O-methyl modification on the second 5' nucleotide and a 5' end phosphate;
        wherein the sense region and the antisense region are capable of forming a duplex of 18-26 base pairs of nucleotides that has at least 80% complementarity over the range of the duplex, and wherein nucleotides of the sense strand and antisense strand other than the first 5' sense nucleotide, the second 5' sense nucleotide, and the second 5' antisense nucleotide include a 2'-OH;

solublizing or resuspending the dried test gene silencing composition in the aqueous medium;

adding cells to the first test well under conditions that permit transfection;

adding cells to a first control well with a dried control composition under conditions that permit transfection, wherein, the dried control composition in the first control well includes at least one of no siRNA, a positive control siRNA that is capable of targeting a known gene, a non-targeting negative control siRNA, an siRNA having at least one toxic motif, a non-functional siRNA, an siRNA that inhibits being taken in and processed by RISC, or a control siRNA that includes a fluorescent marker, the dried control composition being capable of being solublized or resuspended in an aqueous medium;

comparing the effect of the control composition and the test siRNAs on the cells in the first test well and the first control well.

18. A method as in claim 1, further comprising adding at least one cationic polynucleotide carrier to the control well and/or the test well, wherein the cationic polynucleotide carrier is added either before adding the aqueous medium, with the aqueous medium, or after adding the aqueous medium.

19. A method as in claim 18, wherein the cationic polynucleotide carrier includes at least one of a cationic lipid, a polymer, a lipo-polymer, or a lipid-peptide mixture.

20. A method as in claim 17, wherein the dried test gene silencing composition includes a pool of four siRNAs.

21. A method as in claim 17, wherein the test siRNA in the dried test gene silencing composition includes at least one of a conjugate or a hairpin structure.

22. A method as in claim 17, further comprising adding at least one cationic polynucleotide carrier to the control well and/or the test well, wherein the cationic polynucleotide carrier is added either before adding the aqueous medium, with the aqueous medium, or after adding the aqueous medium.

23. A method as in claim 22, wherein the cationic polynucleotide carrier includes at least one of a cationic lipid, a polymer, a lipo-polymer, or a lipid-peptide mixture.

* * * * *